US005721253A

United States Patent [19]

Hartman et al.

[11] Patent Number: 5,721,253

[45] Date of Patent: Feb. 24, 1998

[54] FIBRINOGEN RECEPTOR ANTAGONISTS

[75] Inventors: George D. Hartman, Lansdale; Melissa S. Egbertson, Ambler; Wasyl Halczenko; Ben Askew, both of Lansdale, all of Pa.

[73] Assignee: Merck & Co., Inc., Rahway, N.J.

[21] Appl. No.: 717,952

[22] Filed: Sep. 23, 1996

Related U.S. Application Data

[60] Division of Ser. No. 416,770, May 31, 1995, Pat. No. 5,559,127, which is a continuation-in-part of Ser. No. 960,668, Oct. 14, 1992, abandoned.

[51] Int. Cl.$^6$ ...................... A61K 31/445; C07D 401/06; C07D 401/12; C07D 405/06

[52] U.S. Cl. .......................... 514/323; 514/183; 514/210; 514/318; 514/320; 514/321; 514/322; 514/324; 546/193; 546/195; 546/196; 546/197; 546/198; 546/199; 546/201; 546/202; 546/209; 546/270; 546/271; 546/273; 546/274

[58] Field of Search .................................... 546/193, 195, 546/197, 198, 199, 201, 202, 209, 270, 271, 273, 274; 540/483, 200; 548/221, 222, 161, 163, 165, 171, 178, 179, 180, 304.4, 306.4, 308.4, 307.1, 309.7, 306.1, 307.4, 336.1, 517, 518, 530, 537, 540; 549/462, 467, 466, 468, 29, 51, 58; 514/183, 210, 318, 320, 321, 322, 323, 324, 337, 338, 339, 367, 375, 394, 395, 397, 443, 469, 470

[56] References Cited

PUBLICATIONS

Hartman GD et al. J. Med. Chem. 35, 4640–4642, 1992.

Ford–Hutchinson AW. et al. Can. J. Physiol. Pharmacol. 67, 989–993, 1989.

*Primary Examiner*—Alan L. Rotman
*Assistant Examiner*—Evelyn Huang
*Attorney, Agent, or Firm*—Richard S. Parr; Melvin Winokur

[57] ABSTRACT

Fibrinogen receptor antagonists of the formula:

R12 (O)0-2 D X—Y— E —A—B are disclosed for use in inhibiting the binding of fibrinogen to blood platelets and for inhibiting the aggregation of blood platelets.

5 Claims, No Drawings

FIBRINOGEN RECEPTOR ANTAGONISTS

This is a division of application Ser. No. 08/416,770 filed May 31, 1995 now U.S. Pat. No. 5,559,127, which is the national phase of PCT/US93/09730, filed on Oct. 12, 1993, which is Continuation In Part of Ser. No. 07/960668, filed on Oct. 14, 1992, abandoned.

FIELD OF THE INVENTION

This invention relates to the discovery of fibrinogen receptor antagonists of Formula I for use in inhibiting the binding of fibrinogen to blood platelets and inhibiting the aggregation of blood platelets when administered to mammals, preferably humans.

BACKGROUND OF THE INVENTION

The interaction of platelets with the coagulation and fibrinolytic systems in the maintenance of hemostasis may become pathogenic, requiring prevention and treatment. The fibrinogen receptor antagonists of Formula I are useful in treating various diseases related to platelet aggregation and fibrin formation.

An interest in platelet inhibitors has reemerged as a result of a better understanding of the role of platelets and thrombosis in the pathogenesis of vascular disease, including unstable angina, acute myocardial infarction and stroke.

Platelets are cell-like anucleated fragments, found in the blood of all mammals which participate in blood coagulation. Fibrinogen is a glycoprotein present as a normal component of blood plasma. Fibrinogen participates in platelet aggregation and fibrin formation in the blood clotting mechanism. Platelets are deposited at sites of vascular injury where multiple physiological agonists act to initiate platelet aggregation culminating in the formation of a platelet plug to minimize blood loss. If the platelet plug occurs in the lumen of a blood vessel, normal blood flow is impaired.

Platelet membrane receptors are essential in the process of platelet adhesion and aggregation. Interaction of fibrinogen with a receptor on the platelet membrane complex IIb/IIIa is known to be essential for normal platelet function.

Zimmerman et al., U.S. Pat. No. 4,683,291, describes peptides having utility in the study of fibrinogen-platelet, platelet-platelet, and cell-cell interactions. The peptides are described as having utility where it is desirable to retard or prevent formation of a thrombus or clot in the blood.

Pierschbacher et al., U.S. Pat. No. 4,589,881, describes the sequence of an 11.5 kDal polypeptide fragment of fibronectin which embodies the cell-attachment-promoting activity of fibronectin.

Ruoslahti et al., U.S. Pat. No. 4,614,517, describes tetrapeptides which alter cell-attachment activity of cells to various substrates. Ruoslahti et al., U.S. Pat. No. 4,578,079, describes similar tetrapeptides having Ser substituted with Thr or Cys.

Pierschbacher et al., *Proc. Natl. Acad. Sci. USA*, Vol. 81, pp. 5985–5988, October, 1984, describe variants of the cell recognition site of fibronectin that retain attachment-promoting activity. Pierschbacher et. al. further assayed the cell attachment-promoting activities of a number of structures closely resembling the Arg-Gly-Asp-Ser peptide, and found "that the arginine, glycine, and aspartate residues cannot be replaced even with closely related amino acids, but that several amino acids can replace serine without loss of activity."

Ruoslahti et al., *Science*, Vol. 238, pp. 491–497, Oct. 23, 1987, discuss cell adhesion proteins. They specifically state that "elucidation of the amino acid sequence of the cell-attachment domain in fibronectin and its duplication with synthetic peptides establish the sequence Arg-Gly-Asp (RGD) as the essential structure recognized by cells in fibronectin."

Cheresh, *Proc. Natl. Acad. Sci. USA*, Vol. 84, pp. 6471–6475, September 1987, describes the Arg-Gly-Asp-directed adhesion receptor involved in attachment to fibrinogen and the von Willebrand Factor.

Adams et al., U.S. Pat. No. 4,857,508, describes tetrapeptides which inhibit platelet aggregation and the formation of a thrombus.

Tjoeng et al., EP 352,249, describe platelet aggregation inhibitors which antagonize interactions between fibrinogen and/or extracellular matrix proteins and the platelet gpIIb/IIIa receptor, including 8-guanido-octanoyl-Asp-2-(4-methoxyphenyl)ethyl amide.

Alig et al., EP 372,486, describe N-aryl beta-amino acids which inhibit fibrinogen, fibronectin and von Willebrand factor to the blood platelet fibrinogen receptor (glycoprotein IIb/IIIa).

Alig et al., EP 381,033, describe di-aryl or heteroaryl substituted alkanoic acid derivatives of a defined formula which inhibit binding of proteins to their specific receptors on cell surfaces, including fibrinogen.

Alig et al., EP 384,362, describe glycine peptides of a specified formula containing an amidine group which inhibit binding of fibrinogen to platelet fibrinogen receptors.

Horwell et al., EP 405,537, describe N-substituted cycloalkyl and polycycloalkyl alpha-substituted Trp-Phe- and phenethylamine derivatives which are useful for treating obesity, hypersecretion of gastric acid in the gut, gastrin-dependent tumors, or as antipsychotics.

It is an object of the present invention to provide fibrinogen receptor antagonists for use in inhibiting the binding of fibrinogen to blood platelets and inhibiting the aggregation of blood platelets. Another aspect of the present invention is to provide novel fibrinogen receptor antagonist compounds. Other objects of the present invention are to provide methods of inhibiting the binding of fibrinogen to blood platelets and inhibiting the aggregation of blood platelets, through the administration of novel fibrinogen receptor antagonist compounds. The above and other objects are accomplished by the present invention in the manner described below.

SUMMARY OF THE INVENTION

The present invention provides fibrinogen receptor antagonist compounds of the formula:

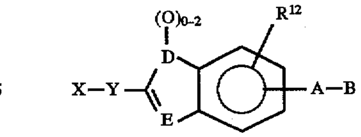

or

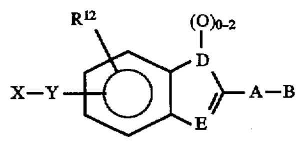

and their pharmaceutically acceptable salts, where D and E are independently chosen from C, N, O, and S;

X is chosen from

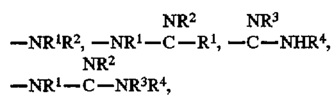

and a 5- to 6-membered mono- or bicyclic aromatic or nonaromatic ring system containing 0, 1, or 2 heteroatoms selected from N, O and S and either unsubstituted or substituted with $R^1$, $R^2$, $R^3$, or $R^4$, wherein $R^1$, $R^2$, $R^3$ and $R^4$ are independently selected from the group consisting of hydrogen, $C_{1-10}$ alkyl, aryl $C_{0-8}$ alkyl, oxo, thio, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy and hydroxy $C_{0-6}$ alkyl;

Y and A are independently chosen from

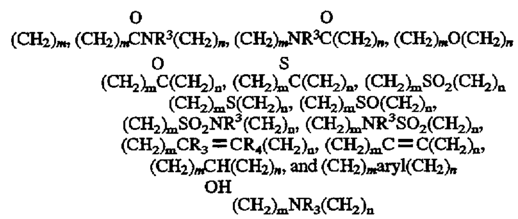

where m and n are integers independently chosen from 0–6;

B is chosen from

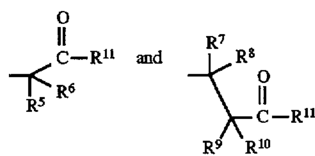

where $R^5$, $R^6$, $R^7$, $R^8$, $R^9$, and $R^{10}$ are independently chosen from:

hydrogen, flourine, $C_{1-8}$ alkyl, hydroxyl, hydroxy $C_{1-6}$ alkyl, carboxy $C_{0-6}$ alkyl, $C_{1-6}$ alkyloxy, $C_{3-8}$ cycloalkyl, aryl $C_{0-6}$ alkyl, $C_{1-6}$ alkylcarbonyloxy, $C_{0-6}$ alkylamino $C_{0-6}$ alkyl, aryl $C_{0-6}$ alkylamino $C_{0-6}$ alkyl, $C_{0-6}$ dialkylamino $C_{0-6}$ alkyl, aryl $C_{0-6}$ alkylcarbonyloxy, $C_{1-8}$ alkylsulfonylamino $C_{0-6}$ alkyl, $C_{1-6}$ alkylaminocarbonyloxy, aryl $C_{0-6}$ alkylaminocarbonyloxy, aryl $C_{0-8}$ alkylsulfonylamino $C_{0-6}$ alkyl, $C_{1-8}$ alkyloxycarbonylamino $C_{0-8}$ alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonyl $C_{0-6}$ alkyl, aryl $C_{0-8}$ alkylaminocarbonyl $C_{0-6}$ alkyl, $C_{0-8}$ alkylaminocarbonyl-amino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl, and aryl $C_{0-6}$ alkylthiocarbonylamino $C_{0-6}$ alkyl, wherein groups may be unsubstituted or substituted with one or more substiuents selected from $R^1$ and $R^2$, and

O
C-AA where AA is an L- or D-amino acid, or its corresponding ester, connected through an amide linkage;

$R^{11}$ is chosen from:

hydroxy, $C_{1-8}$ alkyloxy, aryl $C_{0-6}$ alkyloxy, $C_{1-8}$ alkylcarbonyloxy $C_{1-4}$ alkyloxy, aryl $C_{1-8}$ alkylcarbonyloxy $C_{1-4}$ alkyloxy, and an L- or D-amino acid joined by an amide linkage and wherein the carboxylic acid moiety of said amino acid is as the free acid or is esterified by $C_{1-6}$ alkyl; and $R^{12}$ is chosen from the group described by $R^1$.

Compounds of the invention are useful for inhibiting the binding of fibrinogen to blood platelets and for inhibiting the aggregation of blood platelets. The above-mentioned compounds can be used in a method of acting upon a fibrinogen receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of such compound is another feature of this invention.

DETAILED DESCRIPTION OF THE INVENTION

Fibrinogen receptor antagonist compounds of Formula I are useful in a method of inhibiting the binding of fibrinogen to blood platelets and for inhibiting the aggregation of blood platelets. Fibrinogen receptor antagonists of this invention are illustrated by compounds having the formula:

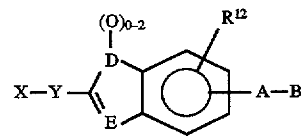

or

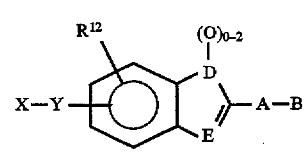

and their pharmaceutically acceptable salts, where D and E are independently chosen from C, N, O, and S;

X is chosen from:

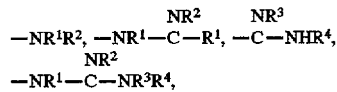

and a 5- to 6-membered mono- or bicyclic aromatic or nonaromatic ring system containing 0, 1, or 2 heteroatoms selected from N, O, and S and either unsubstituted or substituted with $R^1$, $R^2$, $R^3$, or $R^4$, wherein $R^1$, $R^2$, $R^3$, and $R^4$ are independently selected from the group consisting of hydrogen, $C_{1-10}$ alkyl, aryl $C_{0-8}$ alkyl, oxo, thio, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy, and hydrogen $C_{0-6}$ alkyl;

Y and A are independently chosen from

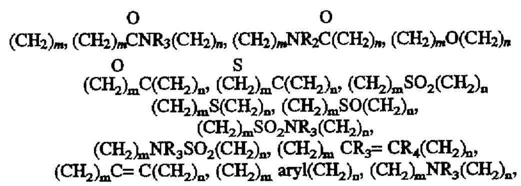

where m and n are integers independently chosen from 0–6;

B is chosen from

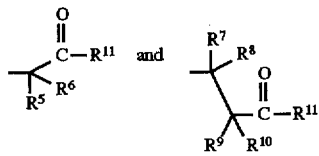

and their pharmaceutically acceptable salts, where $R^5$, $R^6$, $R^7$, $R^8$, $R^9$, and $R^{10}$ are independently chosen from:

hydrogen, flourine, $C_{1-8}$ alkyl, hydroxyl, hydroxy $C_{1-6}$ alkyl, carboxy $C_{0-6}$ alkyl, $C_{1-6}$ alkyloxy, $C_{3-8}$ cycloalkyl, aryl $C_{1-6}$ alkyloxy, aryl $C_{0-6}$ alkyl, $C_{1-6}$ alkylcarbonyloxy, $C_{0-6}$ alkylamino $C_{0-6}$ alkyl, aryl $C_{0-6}$ alkylamino $C_{0-6}$ alkyl, aryl $C_{0-6}$ alkylcarbonyloxy, $C_{0-6}$ dialkylamino $C_{0-6}$ alkyl, $C_{1-6}$ alkylaminocarbonyloxy, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonlyamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl, aryl $C_{0-6}$ alkylthiocarbonylamino $C_{0-6}$ alkyl, $C_{0-8}$ alkylaminocarbonyl $C_{0-6}$ alkyl, and aryl $C_{0-8}$ alkylaminocarbonyl $C_{0-6}$ alkyl, wherein groups may be unsubstituted or substituted with one or more substituents selected from $R^1$ and $R^2$; and

O
C-AA where AA is an L- or D-amino acid, or its corresponding ester, connected through an amide linkage;

$R^{11}$ is chosen from hydroxy, $C_{1-8}$ alkyloxy, aryl $C_{0-6}$ alkyloxy, $C_{1-8}$ alkylcarbonyloxy $C_{1-4}$ alkyloxy, aryl $C_{1-8}$ alkylcarbonyloxy $C_{1-4}$ alkyloxy, and an L- or D-amino acid joined by an amide linkage and wherein the carboxylic acid moiety of said amino acid is as the free acid or is esterified by $C_{1-6}$ alkyl; and $R^{12}$ is chosen from the group described by $R^1$.

A preferred embodiment of the present invention are the compounds

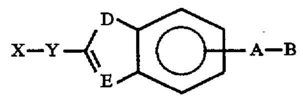

and the pharmaceutically acceptable salts, where D and E are independently chosen from O, N, C and S;

X is chosen from

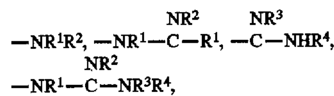

or a 5- to 6-membered mono- or bicyclic nonaromatic ring system containing 0, 1, or 2 heteroatoms selected from N, O, and S and either unsubstituted or substituted with $R^1$, $R^2$, $R^3$ or $R^4$, wherein $R^1$, $R^2$, $R^3$ and $R^4$ are independently selected from the group consisting of hydrogen, $C_{1-10}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy, and hydroxy $C_{0-6}$ alkyl;

Y and A are independently chosen from

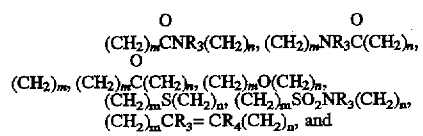

where m and n are integers independently chosen from 0–6;

B is chosen from

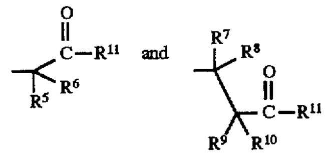

where $R^5$, $R^6$, $R^7$, $R^8$, $R^9$, and $R^{10}$ are independently chosen from:

hydrogen, flourine $C_{1-8}$ alkyl, hydroxyl, hydroxy $C_{1-6}$ alkyl, carboxy $C_{0-6}$ alkyl, $C_{1-6}$ alkyloxy, $C_{3-8}$ cycloalkyl, aryl $C_{0-6}$ alkyl, $C_{1-6}$ alkylcarbonyloxy, $C_{0-6}$ alkylamino $C_{0-6}$ alkyl, aryl $C_{0-6}$ alkylcarbonyloxy, $C_{0-6}$ dialkylamino $C_{0-6}$ alkyl, $C_{1-6}$ alkylaminocarbonyloxy, aryl $C_{1-6}$ alkylaminocarbonyloxy, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$ alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl, aryl $C_{0-6}$ alkylthiocarbonylamino $C_{0-6}$ alkyl wherein groups may be unsubstituted or substituted with one or more substituents selected form $R^1$ and $R^2$; and

O
C-AA where AA is an L- or D-amino acid, or its corresponding ester, connected through an amide linkage; and $R^{11}$ is chosen from hydroxy, $C_{1-8}$ alkyloxy, aryl $C_{0-6}$ alkyloxy, $C_{1-8}$ alkylcarbonyloxy $C_{1-4}$ alkyloxy, aryl $C_{1-8}$ alkylcarbonyloxy $C_{1-4}$ alkyloxy, and an L- or D-amino acid joined by an amide linkage and wherein the carboxylic acid moiety of said amino acid is as the free acid or is esterified by $C_{1-6}$ alkyl.

A more preferred embodiment of the present invention are the compounds

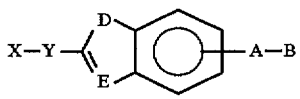

where D and E are independently chosen from C, N, O and S;

X is chosen from

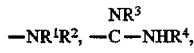

and a 5- to 6-membered mono- or bicyclic nonaromatic ring system containing 0, 1, or 2 heteroatoms selected from N, O and S and either unsubstituted or substituted with $R^1$, $R^2$, $R^3$ or $R^4$, wherein $R^1$, $R^2$, $R^3$ and $R^4$ are independently selected from the group consisting of hydrogen, $C_{1-10}$ alkyl, $C_{1-4}$ alkoxy $C_{0-6}$ alkyl, Y and A are optional substituents that are independently chosen from

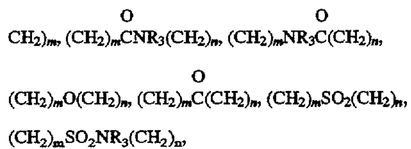

where m and n are integers independently chosen from 0–6;

B is

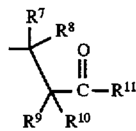

where $R^7$, $R^8$, $R^9$, and $R^{10}$ are independently chosen from: hydrogen, fluorine, $C_{1-8}$ alkyl, hydroxyl, hydroxy $C_{1-6}$ alkyl, carboxy $C_{0-6}$ alkyl $C_{1-6}$ alkyloxy, $C_{1-6}$ alkylcarbonyl, $C_{3-8}$ cycoalkyl, aryl $C_{0-6}$ alkylcarbonyl, aryl $C_{0-6}$ alkyl, $C_{1-6}$ alkylcarbonyloxy, $C_{0-6}$ alkylamino $C_{0-6}$ alkyl, aryl $C_{0-6}$ alkylcarbonyoxy, $C_{0-6}$ dialkylamino $C_{0-6}$ alkyl, $C_{1-6}$ alkylaminocarbonyloxy, $C_{1-8}$ alkylsulfonylamino $C_{0-6}$ alkyl, aryl $C_{0-6}$ alkylsulfonylamino $C_{0-6}$ alkyl, $C_{1-8}$ alkylsulfonylamino $C_{0-6}$ alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, and $C_{1-6}$ alkylthiocarbonylamino $C_{0-6}$ alkyl; and $R^{11}$ is chosen from hydroxy, $C_{1-8}$ alkyloxy, and aryl $C_{0-6}$ alkyloxy.

The term "aryl" means a mono-or bicyclic system composed of 5- and 6-membered aromatic rings containing 0, 1, or 2 heteroatoms chosen from N, O or S.

The term "alkyl" means straight or branched alkane, alkene or alkyne. The term "alkoxy" includes an alkyl portion where alkyl is as defined above.

The terms "arylalkyl" and "alkylaryl" include an alkyl portion where alkyl is as defined above and an aryl portion where aryl is as defined above. The $C_{0-n}$ or $C_{1-n}$ designation, where n may be an integer from 1–10 or 2–10 respectively, refers to the alkyl component of the arylalkyl or alkylaryl unit.

The term "halogen" includes fluorine, chlorine, iodine and bromine.

The term "oxy" means an oxygen (O) atom. The term "thio" means a sulfur (S) atom. Under standard nomenclature used throughout this disclosure, the terminal portion of the designated side chain is described first followed by the adjacent functionality toward the point of attachment. For example, a $C_{1-6}$ alkyl substituted with $C_{1-6}$ alkylcarbonylamino is equivalent to

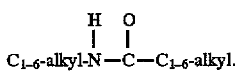

Most preferred compounds of the invention, with corresponding $IC_{50}$ values for some of these in parentheses, are:

2-(Butylsulfonylamino)-3-{5[2'-(4-piperidin-4-yl-propyl) benzofuranyl]}propanoic acid ($IC_{50}$=0.20 μM);

2-(Butylsulfonylamino)-3-{5-[2'-(4-piperidin-4-yl-methyl) aminocarbonyl]benzofuranyl}propionic acid ($IC_{50}$=6.6 μM);

2-[2-(Piperidin-4-yl)ethyl]benzothiophene-6-N-[3-(2(S)-N-carbobenzyloxyaminopropionic acid)carboxamide ($IC_{50}$=0.067 μM);

2-[2-(Piperidin-4-yl)ethyl]benzothiophene-6-N-[3-(2(S)-N-butylsulfonylaminopropionic acid)carboxamide ($IC_{50}$=0.036 μM);

2-[2-(Piperidin-4-yl)ethyl]benzothiophene-S,S-dioxide-6-N-[3-(2(S)-N-butylsulfonylaminopropionic acid) carboxamide;

2-[2-(Piperidin-4-yl)ethyl]benzothiophene-6-N-[3-(2-(S)-N-Methylsulfonylaminopropionic acid)]carboxamide;

2-[2-(4-Piperidinyl)ethyl]benzimidazole-5-carbonyl-[2(S)-p-toluenesulfonylamino]-β-alanine;

2-[2-(4-Piperidinyl)ethyl]benzimidazole-5-carbonyl-[2(S)-butylsulfonylamino]-β-alanine ($IC_{50}$=0.022 μM); and 5-[2-[4-Piperidinylethyl)oxy]-2-indolecarbonyl-2(S)-phenylsulfonylamino-β-alanine ($IC_{50}$=0.012 μM), and 2-[Z-(Piperidin-4-yl)ethyl]benzothiophene-6-N-[3-(2-(S)-benzylureido)propionic acid]carboxamide.

The ADP-stimulated platelet aggregation assay was used to determine $IC_{50}$ inhibition associated with compounds of the invention.

Human platelets were isolated from fresh blood, collected into acid citrate/dextrose by differential centrifugation followed by gel filtration on Sepharose 2B in divalent ion-free Tyrode's buffer (pH 7.4) containing 2% bovine serum albumin. Platelet aggregation was measured at 37° C. in a a Chronolog aggregometer. The reaction mixture contained gel-filtered human platelets ($2\times10^8$ per 1), fibrinogen (100 μg/ml), $Ca^{2+}$ (1 mM), and the compound to be tested. Aggregation was initiated by adding 10 uM ADP 1 minute after the other components had been added. The reaction was allowed to proceed for at least 2 minutes. The extent of inhibition of aggregation was expressed as the percentage of the rate of aggregation observed in the absence of inhibitor. The $IC_{50}$ is the dose of a particular compound inhibiting aggregation by 50% relative to a control lacking the compound.

The abbreviations listed below are defined as Bn, benzyl; NMM, N-methylmorpholine; HOBt, 1-hydroxybenzotriazole; EDC, 1-(3-dimethylamino-propyl) -3-ethylcarbodiimide hydrochloride; DMF, dimethylformamide; Pib, 4-(4-piperidyl)butanoyl; pTSA, paratoluenesulfonic acid; DMS, dimethylsulfide; TFA, trifluoroacetic acid; THF, tetrahydrofuran; DIBAL, diisobutylaluminum hydride; Boc (or BOC), tert-butoxycarbonyl; Cbz, benzyloxycarbonyl; Suc, succinoyl; alpine borane, β-isopinocamphenyl-9-borabicyclo[3.3.1]-nonane; TBDMS, tert-butyldimethylsilyl; Jones reagent, chromic acid; NBS, N-Bromosuccinimide; DEAD, diethyl azodicarboxylate; BPO, Benzoyl peroxide; $PPh_3$, triphenyl phosphine; DMSO, Dimethylsulfoxide; $Et_3N$, triethylamine; $Tf_2O$, triflic anhydride; DMAP, 4-dimethylamino-pyridine; BOP, benzotriazol-1-yloxytris(dimethylamino) phosphonium hexafluorophosphate; PhCHO, benzaldehyde; and $Boc_2O$, di-t-butyldicarbonate; dppp, 1,3-bis (diphenylphosphino)propane; $TMSCHN_2$, trimethylsilyl diazomethane; EtOAc, ethyl acetate; $CH_2Cl_2$, methylene chloride; HOAc, acetic acid; $CH_3OH$, methanol; $CHCl_3$, chloroform; AA is an L- or D-amino acid chosen from naturally occurring amino acids glycine, alanine, valine, isoleucine, leucine, serine, threonine, proline, aspartic acid, glutamic acid, lysine, arginine, asparagine, glutamine, cysteine, methionine, tryptophan, phenylalanine, tyrosine, and histidine.

Unless otherwise indicated, all degree values are Celsius.

2-(N-t-Butyloxycarbonylpiperidin-4-yl)ethyl iodide, (3-2), used in Scheme 3, is prepared by according to the following procedure.

4-Piperidine-2-ethanol (Aldrich) (130 g, 1.0 mole) was dissolved in 700 mL dioxane, cooled to 0° C. and treated with 3N NaOH (336 mL, 1.0 mole), and di-t-butyldicarbonate (221.8 g, 1.0 mole). The ice bath was removed and the reaction stirred overnight. The reaction was concentrated, diluted with water and extracted with ether. The ether layers were combined, washed with brine, dried over $MgSO_4$, filtered and evaporated to give Boc-4-piperidine-2-ethanol. $R_f$=0.37 in 1:1 EtOAc/Hexanes, ninhydrin stain $^1H$ NMR (300 MHz, $CDCl_3$) δ 4.07 (bs, 2H), 3.7 (bs, 2H), 2.7 (t, J=12.5 Hz, 2H), 1.8–1.6 (m, 6H), 1.51 (s, 9H), 1.1 (ddd, J=4.3, 12.5, 12 Hz, 2H).

Boc-4-piperidine-2-ethanol (10.42 g, 0.048 mole was dissolved in 400 ml benzene and imidazole (4.66 g, 0.068 moles) and triphenylphosphine (15.24 g, 0.05 moles) were added at room temperature. After 6 hours the reaction mixture was filtered and the filtrate was evaporated to give a dark residue. This was purified by flash chromatography on silica gel eluting with 10%-EtOAc-hexanes to give Boc-4-piperidine-2-ethyl iodide as a yellow oil.

The alcohol 1-1 is prepared according to Example 18, pages 21–22, up to line 21, of EP 478 328, prior to THF and triphenylphosphine treatment.

The pharmaceutically acceptable salts of the compounds of Formula I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, peperidine, pyrrolidine, benzylamine and the like, or a quaternary ammonium hydroxide such as tetramethylammonium hydroxide and the like.

The compounds of Formula I are useful in inhibiting the binding of fibrinogen to blood platelets, inhibiting aggregation of blood platelets, treatment of thrombus formation or embolus formation, and in the prevention of thrombus formation or embolus formation. These compounds are useful as pharmaceutical agents for mammals, especially for humans. The compounds of this invention may be administered to patients where prevention of thrombosis by inhibiting binding of fibrinogen to the platelet membrane glycoprotein complex IIb/IIIa receptor is desired. Compounds of this invention may also be used to prevent or modulate the progress of myocardial infarction, unstable angina and thrombotic stroke, in either acute or chronic settings. In addition, they may be useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gpIIb/IIIa on the platelet membranes and fibrinogen adsorbed to the surface of the circuit. (Gluszko et al., *Amer. J. Physiol.*, 1987, 252:H, pp 615–621). Platelets released from artificial surfaces show impaired hemostatic function. Compounds of this invention may be administered to prevent adhesion.

Other applications of these compounds include prevention of platelet thrombosis, thromboembolism, reocclusion, and restenosis during and after thrombolytic therapy and prevention of platelet thrombosis, thromboembolism, reocclusion and restenosis after angioplasty of coronary and other arteries and after coronary artery bypass procedures.

The compounds of Formula I may be administered to mammals, preferably in combination with pharmaceutically-acceptable carriers or diluents, optionally with known adjuvants such as alum, in a pharmaceutical composition which is non-toxic and in a therapeutically effective amount, according to standard pharmaceutical practice. The compounds can be administered orally or parenterally, including intravenous, intramuscular, intraperitoneal, trans-dermal, subcutaneous and topical administration.

For oral use of a fibrinogen receptor antagonist according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added.

For intramuscular, intraperitoneal, subcutaneous, and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment and prevention of diseases related to platelet aggregation, fibrin formation, and thrombus and embolus formation, comprising the administration of a therapeutically effective but non-toxic amount of the compounds of Formula I, with or without pharmaceutically acceptable carriers or diluents.

Compositions of this invention include fibrinogen receptor antagonist compounds of this invention in combination with pharmacologically acceptable carriers, e.g. saline, at a pH level e.g. 7.4, suitable for achieving inhibition of platelet aggregation. The compositions may also be combined with anticoagulants such as heparin or warfarin. The compositions may also be combined with thrombolytic agents such as plasminogen activators or streptokinase in order to inhibit platelet aggregation in more acute settings. The composition may further be combined with antiplatelet agents such as aspirin. The compositions are soluble in an aqueous medium, and may therefore be effectively administered in solution.

When a compound according to Formula I is used as a fibrinogen receptor antagonist in a human subject, the daily dosage will normally be determined by the prescribing physician with the dosage generally varying according to the age, weight, and response of the individual patient, as well as the severity of the patients symptoms.

In one exemplary application, a suitable amount of compound is administered orally to a heart attack victim subsequent to angioplasty. Administration occurs subsequent to angioplasty, and is in an amount sufficient to inhibit platelet aggregation, e.g. an amount which achieves a steady state plasma concentration of between about 0.01–100 μM preferably between about 0.1–50 μM.

The present invention also includes a pharmaceutical composition comprising compounds of the present invention in combination with tissue type plasminogen activator or streptokinase. The invention also includes a method for promoting thrombolysis and preventing reocclusion in a patient which comprises administering to the patient an effective amount of compositions of the invention.

The present invention provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amount of the compounds of this invention, with or without pharmaceutically acceptable carriers or diluents.

The present invention still further provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amount of the compounds of this invention in combination with thrombolytic agents, such as tissue plasminogen activators or streptokinase, anticoagulants such as heparin or warfarin, or antiplatelet agents such as aspirin, with or without pharmaceutically acceptable carriers or diluents.

The compounds of Formula I are prepared according to the reaction schemes set forth below.

SCHEME 1

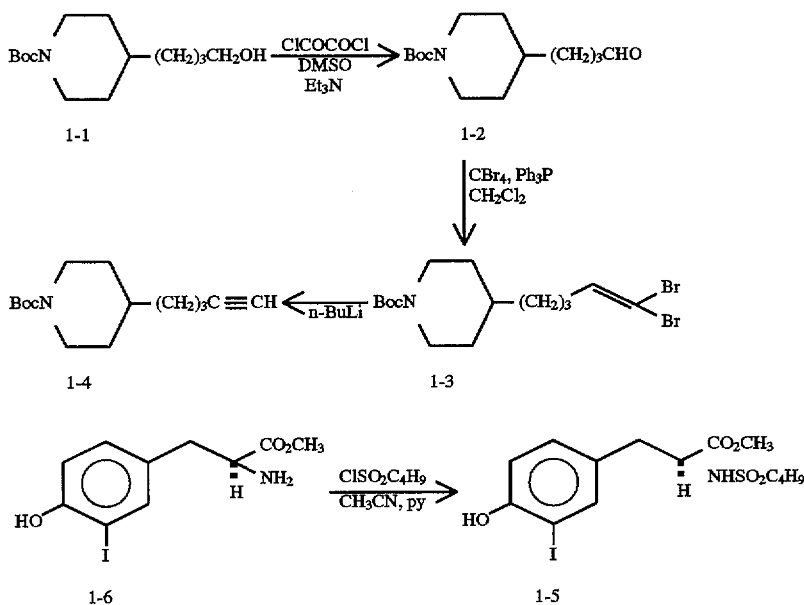

-continued

SCHEME 1

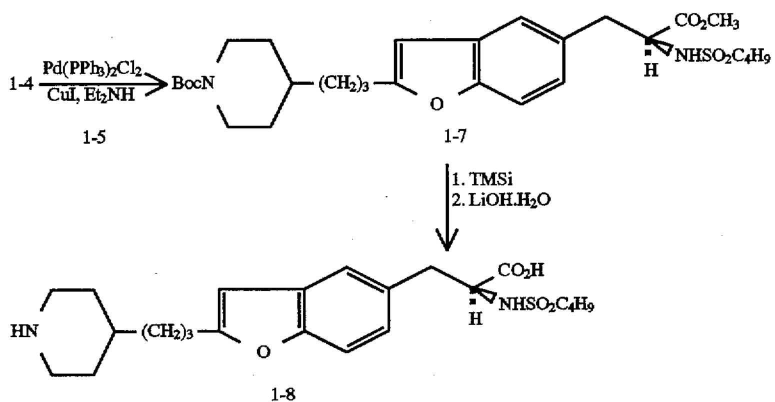

4-(N-t-Butyloxycarbonylpiperidin-4-yl)butanal(1-2)

A solution of oxalyl chloride (8.48 moles) in $CH_2Cl_2$ (60 ml) cooled to −70° was treated with DMSO (11.27 mmoles) and this was stirred for 15 min. A solution of 1-1 (1.45 g, 5.63 mmoles) was added and the resulting mixture stirred for 2 hrs at −70°. Then, triethylamine (28.7 mmoles) was added and the reaction mixture was stirred for 2.0 hrs.

The reaction mixture was washed in $H_2O$, 10% $KHSO_4$ solution, $H_2O$, brine and dried ($Na_2SO_4$). Solvent removal gave 1-2 as an oil.

$^1$H NMR (300 MHz, $CDCl_3$) δ 1.10 (2H,m), 1.23–1.40 (4H,m), 1.45 (9H,s), 1.58–1.74 (4H,m), 2.43 (2H,dt), 2.68 (2H,dt), 4.09 (2H,bd), 9.78 (1H,s).

5-(N-t-Butyloxycarbonylpiperidin-4-yl)-1,1-dibromo-pent-1-ene (1-3)

A solution of $CBr_4$ (3.45 g, 10.42 mmol) in $CH_2Cl_2$ (40 ml) was cooled to 0° and treated with $Ph_3P$ (5.46 g, 20.8 mmol) with stirring for 1.5 hrs. Reaction mixture was then cooled to −70° and treated with 1-2 (1.29 g, 5.08 mmol) in $CH_2Cl_2$ (10 ml) and this was stirred for 0.5 hr.

The reaction was then quenched with $Et_3N$ (4 ml), warmed to room temperature and poured into hexane (500 ml). The suspension was filtered and the filtrate concentrated to provide a residue that was purified by flash chromatography on silica gel eluting with hexane (15)/EtOAc (1) to give pure 1-3.

$^1$H NMR (300 MHz, $CDCl_3$) δ 1.08 (2H,m), 1.20–1.40 (4H,m), 1.45 (9H,s), 1.62 (2H,bd), 2.08 (2H,m), 2.67 (2H,t), 4.06 (2H,d), 6.39 (1H,t).

5-(N-t-Butyloxycarbonylpiperidin-4-yl)pent-1-yne (1-4)

A solution of 1-3 (1.70 g, 4.13 mmol) in THF (80 ml) was cooled to −78° and treated with n-BuLi (4.25 mmol) with stirring for 15 min. The reaction was then quenched with 10% $KHSO_4$ (25 ml) and the solvent was removed. The residue was taken up in $Et_2O$ (150 ml) and this was washed with 10% $KHSO_4$ solution, brine, and dried ($Na_2SO_4$).

Solvent removal gave 1-4 as an oil.

$^1$H NMR (300 MHz, $CDCl_3$) δ 1.10 (2H,m), 1.20–1.40 (4H,m), 1.47 (9H,s), 1.55 (1H,m), 1.64 (2H,bd), 2.08 (1H,q), 2.20 (1H,dt), 2.68 (2H,dt), 4.08 (2H, bd), 6.39 (1H,t).

Methyl 2(S)-(Butylsulfonylamino)-3-(4-hydroxy-3-iodo)-phenylpropionate (1-5)

A solution of 1-6 (3-iodo-L-tyrosine (Aldrich) was converted to 1-6 by treatment with $SOCl_2$/MeOH in the normal fashion) (10.5 g, 0.033 mol) in $CH_3CN$ (150 ml) was treated with pyridine (0.039 mol) and butanesulfonyl chloride (0.039 mmol) and the resulting mixture was heated at 60° for 2 days.

The solvent was removed and the residue was taken up in 10% $KHSO_4$ soln and extracted with EtOAc. The organic extract was dried and the solvent removed to give 1-5.

$^1$H NMR (300 MHz, $CDCl_3$) δ 0.90 (3H,t), 1.35 (1H,m), 1.61 (2H,m), 2.78 (2H,m), 2.89 (1H,m), 3.08 (1H,dd), 3.78 (3H,s), 4.29 (1H,m), 5.10 (1H,m), 5.98 (1H,m) 6.89 (1H,d), 7.08 (1H,d), 7.50 (1H,m).

Methyl 2(S)-(Butylsulfonylamino)-3-{5-[2'-3-(N-t-butyloxycarbonylpiperidin-4-ylpropyl)benzofuranyl]}-propionate (1-7)

A solution of 1-5 (0.485. g, 1.14 mmol) in diethylamine (10 ml) was treated with Pd $(Ph_3P)_2Cl_2$ (0.04 g), cuprous iodide (5.5 mg) and 1.4 (0.34 g, 1.37 mmol) and the resulting mixture was stirred at rt for 72 hrs.

The solvent was removed and the residue purified by flash chromatography in silica gel eluting with hexane (80)/EtOAc (20) to give pure 1-7.

$^1$H NMR (300 MHz, $CDCl_3$) δ 0.77 (t,J=7.3 Hz, 3H), 1.05–1.42 (m, 9H), 1.44 (s, 9H), 1.48–1.77 (m,4H), 2.68 (m, 6H), 3.04 (dd,J=7.6, 13.8 Hz, 1H), 3.23 (dd,J=5.1, 13.8 Hz, 1H), 3.77 (s, 3H), 4.07 (bs, 2H), 4.35 (dd,J=5.1, 7.6 Hz, 1H), 4.5 (bs, 1H), 6.32 (s, 1H), 6.98 (m, 1H), 7.25 (m, 3H).

2(S)-(Butylsulfonylamino)-3-{5-[2'-3-(piperidin-4-ylpropyl)benzofuranyl]}propionic acid (1-8)

A solution of 1-7 (0.18 g, 0.33 mmol) in $CHCl_3$ (20 ml) was treated with TMSI at room temperature. After 15 minutes 10 ml $CH_3OH$ was added, and the solvent was then removed. The residue was taken up in THF (1)/MeOH (1)$H_2O$ (1) (12 ml/and $LiOH.H_2O$ (0.138 g, 3.28 mmol) was added. After 2 hours at room temperature the solvent was removed and the residue was purified by flash chromatography on silica gel eluting with EtOH(9)/$NH_4OH$(1)/$H_2O$(1) to give pure 1-8.

$^1$H NMR (300 MHz, $CD_3OD$) δ 0.78 (t,J=7.3 Hz, 3H), 1.06–1.6 (m, 10H), 1.78 (m,2H), 1.85 (bd, J=14.5 Hz, 2H), 2.68 (m, 2H), 2.75 (m,2H), 2.85 (m, 2H), 2.90 (dd, J=8.3, 13.6 Hz, 1H), 3.20 (dd, J=4.8, 13.6 Hz, 1H), 3.30 (m, 2H), 3.97 (dd, J=4.8, 8.3 Hz, 1H), 6.41 (s, 1H), 7.16 (dd, J=1.8, 8.1 Hz, 1H), 7.27 (d, J=8.1 Hz, 1H) 7.4 (d, J=1.7 Hz, 1H).

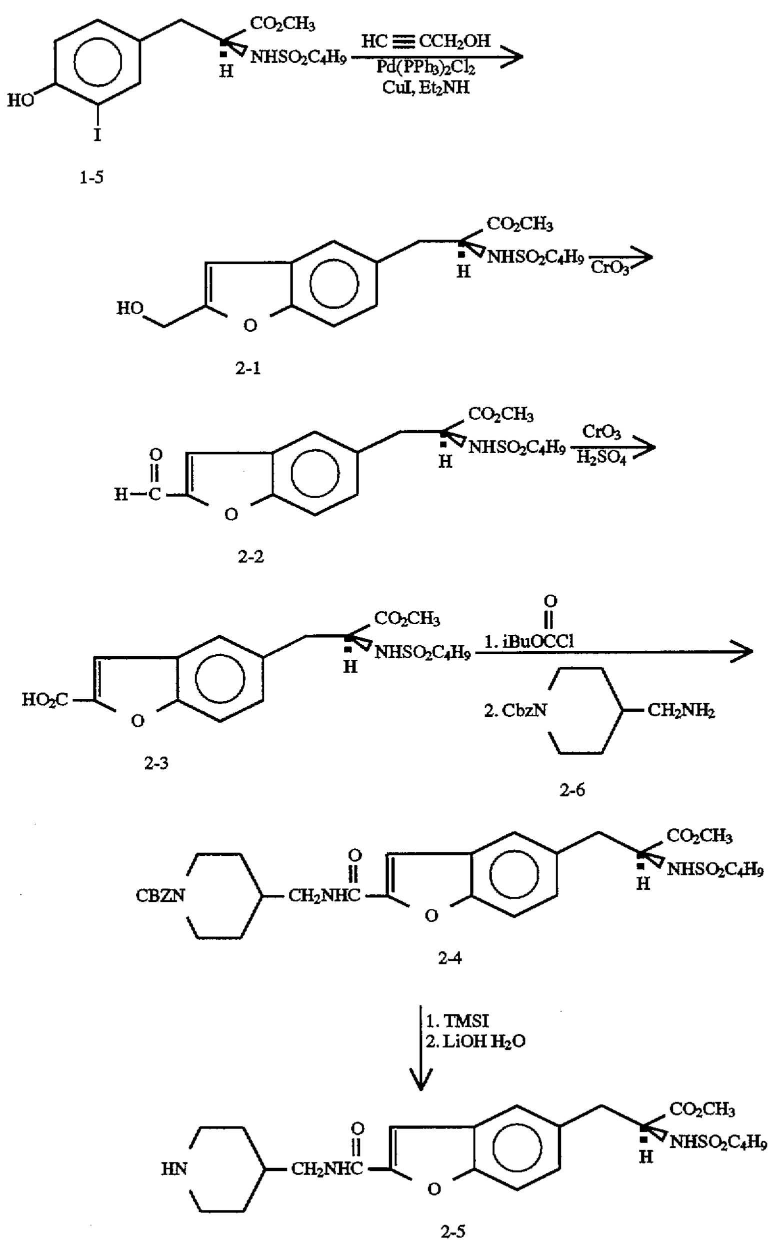

Methyl 2(S)-(Butylsulfonylamino)-3-{5-[2'-(hydroxymethyl)]-benzofuranyl}propionate (2-1)

Propargyl alcohol (2.05 mmol) was dissolved in $Et_2NH$ (5 ml) and treated with 1-5 (0.83 g, 1.95 mmol), $Pd(PPh_3)_2Cl_2$ (0.060 g) and CuI (0.009 g) and the resulting mixture was stirred at room temperature for 4 days. The solvent was removed and the residue purified by flash chromatography on silica gel eluting with hexane (6)/EtOAc(4) to give pure 2-1.

$^1$H NMR (300 MHz, $CDCl_3$) δ 0.80 (3H,t), 1.23 (2H,m), 2.58 (2H,m), 2.00 (1H,m), 2.71 (2H,t), 3.03–3.30 (2H,m), 3.77 (3H,s), 4.40 (1H,m), 6.60 (1H,s), 7.07 (1H,d), 7.38 (2H,m).

Methyl 2(S)-(Butylsulfonylamino)-3-{5-[2'-(formyl)-benzofuranyl]}-propionate (2-2)

A solution of 2-1 (0.050 g, 0.0135 mmol) in $CH_2Cl_2$ (50 ml) was treated at room temperature with $CrO_3$/pyridine (0.081 mmol $CrO_3$ in 10 ml $CH_2Cl_2$ containing 0.63 pyridine). After 1.0 hour the solvent was removed and the residue purified by flash chromatography on silica gel eluting with hexane (1)/EtOAc (1) to give pure 2-2.

$^1$H NMR (300 MHz, $CDCl_3$) δ 0.80 (3H,t), 1.23 (2H,m), 1.57 (2H,m), 2.77 (2H,m), 3.21 (2H,m), 3.79 (3H,s), 4.40 (1H,m), 5.02 (1H,m), 7.35 (1H,dd), 7.58 (3H,m), 9.87 (1H,s),

Methyl 2(S)-(Butylsulfonylamino)-3-{5-[2'-(carboxy)benzofuranyl]}-propionate (2-3)

A solution of 2-2 (0.135 g, 0.0367 mmol) in acetone (10 ml) was treated with $CrO_3/H_2SO_4$ reagent dropwise. After 10 minutes the orange color had disappeared and the reaction was greenish. After 0.5 hr saturated $NaHCO_3$ soln was added to pH=9 and this was extracted in EtOAc. The aqueous phase was then acidified to pH 2-3 with 10% $KHSO_4$ solution and extracted with EtOAc. The organic extract was dried ($Na_2SO_4$) and the solvent removed to give 2-3.

1H NMR (300 MHz, $CDCl_3$) δ 0.83 (3H,t), 1.33 (2H,m), 1.70 (2H,m), 2.93 (2H,m), 3.26 (2H,m), 3.84 (3H,s), 4.55 (1H,bs), 5.75 (1H,bs), 7.22 (1H,m), 7.40 (1H,bs), 7.52 (2H,bs).

Methyl 2(S)-(Butylsulfonylamino)-3-{5-[2'-(4-N-carbobenzyloxy-piperidinylmethyl)aminocarbonyl] benzofuranyl}propionate (2-4)

A solution of 2-3 (0.11 g, 0.29 mmol) in $CH_2Cl_2$ (10 ml) was cooled to 0° and treated with N-methylmorpholine (0.057 mmol) followed by isobutyl chloroformate (0.032 mmol). After stirring at 0° for 10 minutes N-CBZ-(4-aminomethyl)piperidine (2-6) (0.078 g, 0.032 mmoles) was added and reaction was stirred for 1.0 hr. The reaction mixture was quenched with pH 7 buffer and extracted with $CH_2Cl_2$. The organic phase was washed with 10% $KHSO_4$, brine, dried ($Na_{SO4}$) and the solvent was removed to provide 2-4.

$^1$H NMR (300 MHz, $CDCl_3$) δ 0.80 (3H,t), 1.23 (4H,m), 1.58 (2H,m), 1.80 (3H,m), 2.75 (4H,m), 3.07–3.30 (2H,m), 3.57 (2H,m) 3.76 (3H,s) 4.22 (2H,m), 4.38 (1H,m), 4.96 (1H,d), 5.10 (1H,s) 6.75 (1H,t), 7.21–7.50 (9H,m).

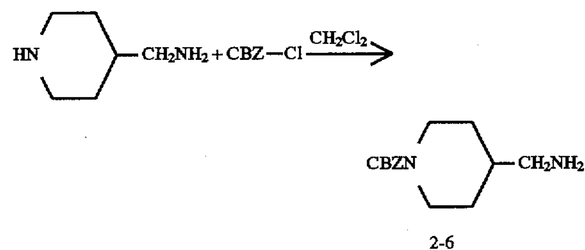

N-CBZ-(4-Aminomethyl)piperidine (2-6)

A solution of 4-(aminomethyl)piperidine (Aldrich) (5.0 g, 0.0438 mol) in $CH_2Cl_2$ (100 ml) was cooled to –78° and treated with CBZ-Cl (Aldrich) (0.022 mol) dropwise. The reaction mixture was stirred at –78° C. for 0.5 hr and then allowed to warm to 0° over 1 hour. The reaction mixture was filtered and the solution concentrated to give a residue that was purified by flash chromatography on silica gel eluting with 5% MeOH/$CHCl_3$+1% $Et_3N$ to give pure 2-6.

$^1$H NMR (300 MHz, $CDCl_3$) δ 1.1 (2H, m), 1.4 (3H, m), 1.7 (2H, bd), 2.57 (2H, d), 2.75 (2H, bt), 4.2 (2H, bs), 5.11 (2H, s), 7.2-7.4 (5H, m).

2(S)-(Butylsulfonylamino)-3-{5-[2'-(4-piperidinylmethyl)amino-carbonyl] benzofuranyl}propionic acid (2-5)

A soln of 2-4 (0.13 g, 0.21 mmol) in $CH_2Cl_2$ (10 ml) was treated with TMSI (2.5 mmol) at room temperature for 0.5 hr. Methanol (5 ml) was then added with stirring and the solvent was removed. The residue was taken up in THF (1)/MeOH (1)/$H_2O$(1) (12 ml) and $LiOH.H_2O$ (0.088 g, 2.1 mmol) was added. After stirring for 1.0 hr. at room temperature the solvent was removed and the residue was purified by flash chromatography on silica gel eluting with EtOH(1)/$H_2O$ (1)/MeOH (1) to give pure 2-5.

$^1$H NMR (300 MHz, $CD_3OD$) δ 0.82 (t, J=7.3Hz, 3H), 1.26 ((m, 2H), 1.4–1.6 (m, 4H), 2.0 (bd, 14.5 Hz, 3H), 2.8 (m, 2H), 3.0 (m, 3H), 3.20 (m, 1H), 3.3–3.5 (m, 4H), 3.99 (dd, J=4.8, 7.9 Hz, 1H), 7.3–7.5 (m, 3H), 7.6 (s, 1H).

SCHEME 3

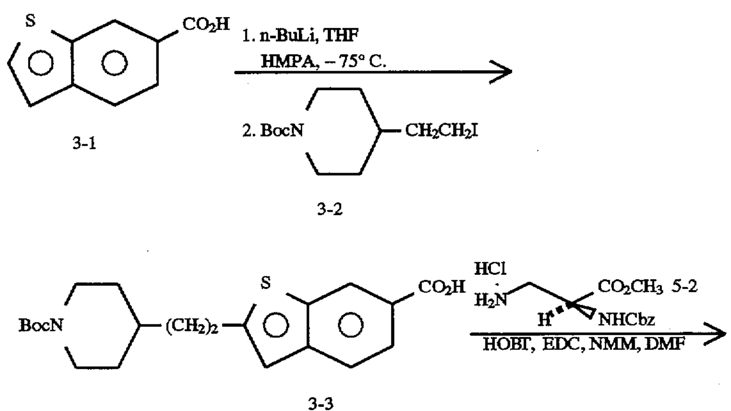

-continued

SCHEME 3

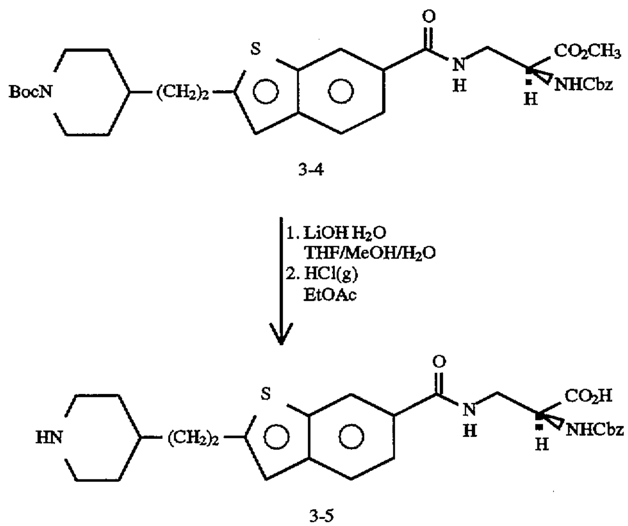

2-[2-(n-t-Butyloxycarbonylpiperidin-4-yl)ethyl] benzothiophene-6-carboxylic acid (3-3)

A solution of benzothiophene-6-carboxylic acid (1.78 g, 0.01 mol) in THF (140 ml) cooled to −75° was treated with n-BuLi (0.02 mol) dropwise and the resulting solution was stirred at −70° for 1 hr. Then, a solution of 2-(N-t-Butyloxycarbonylpiperidin-4-yl)ethyl iodide (3.39 g, 0.01 mol) in THF (10 ml) was added dropwise followed by HMPA (1.79 g, 0.01 mol). The resulting solution was stirred at −70° for 4 hrs and then at 23° for 16 hrs. The cooled reaction was quenched with 10% $KHSO_4$, the solvent removed, and the residue was taken up in $H_2O$ (150 ml) and extracted with EtOAc. The solvent was removed and the residue was purified by flash chromatography on silica gel eluting with $CHCl_3$(97)/MeOH (2)/HOAC (1) to give a solid which was identified to be a mixture of 3-1 and 3-3.

These were separated to by a sequence that involved conversion to the methyl ester, column chromatography [(silica, hexane(4)/EtOAC (1)], and hydrolysis (LiOH.$H_2O$) to give pure 3-3.

$^1$H NMR (300 MHz, $CDCl_3$) δ 1.20 (3H, m), 1.42 (9H, s), 1.50 (2H, m), 1.72 (4H, m) 2.68 (2H, m), 2.97 (2H, m, 4.12 (2H, m), 7.09 (1H, s), 7.72 (1H, d), 8.05 (1H, d). 2-[2-(N-t-Butyloxycarbonylpiperidin-4-yl)ethyl]benzothiophene-6-N-[3-(methyl 2(S)-N-carbobenzyloxyaminopropionate)] carboxamide (3-4)

A solution of 3-3 (0.44 g, 0.0011 mol), 5-2 (0.329 g, 0.0014 mol), and HOBT (0.17 g, 0.0012 mol) in DMF (20 ml) at ambient temperature was treated with N-methylmorpholine (NMM), (0.34 g, 0.0034 mol) followed by EDC (0.25 g, 0.0013 mol). After stirring overnight, the solvent was removed and the residue was taken up in EtOAc (200 ml) and washed with 10% $KHSO_4$ solution, brine, saturated $NaHCO_3$ solution and dried ($NaSO_4$). The solvent was removed and the residue purified by flash chromatography on silica gel eluting with hexane(55)/EtOAc(45) to give pure 3-4 as a solid.

$R_f$ 0.35, silica, hexane(1)/EtOAc(1)

$^1$H NMR (300 MHz, $CDCl_3$) 1.20 (2H,m), 1.43 (9H,s), 1.50 (2, H,m) 1.73 (4H,m), 2.75 (2H,bt), 2.95 (2H,t), 3.78 (2H,s), 3.98 (2H,m), 4.08 (2H,m), 4.56 (1H,m), 5.11 (2H,s), 5.96 (1H,d), 7.03 (1H,s), 7.31 (2H,m), 7.63 (1H,m).

2-[2-(Piperidin-4-yl)ethyl]benzothiophene-6-N-[3-(2 (S)-N-carbobenzyloxyaminopropionic acid)] carboxamide (3-5)

A solution of 3-4 (0.12 g, 0.19 mmol) in THF (1)/MeOH (1)/$H_2O$ (1) (10 ml) was treated at 23° with LiOH.H2O (0.024 g, 0.58 mmol) for 18 hrs. The solvent was removed and the residue was taken up in $H_2O$ (50 ml), acified to pH 2-3 with 10% $KHSO_4$ soln, and extracted with EtOAc. The extract was dried ($Na_2SO_4$), the solvent removed, and the residue purified by flash chromatography on silica gel eluting with $CHCl_3$(95)/MeOH(5)/HOAC (1) to give the desired acid, $R_f$ 0.25 (silica, $CHCl_3$(95)/MeOH(5)/HOAC (1). This acid was dissolved in EtOAc (25 ml), cooled to −25° and treated with HCl (g) for 15 min and then stirred at 0° for 1 hr. The solvent was removed and the residue was tritated with EtOAc to give pure 3-5. $R_f$ 0.3 [(silica, EtOH(9)/$H_2O$ (1)/$NH_4OH$ (1)].

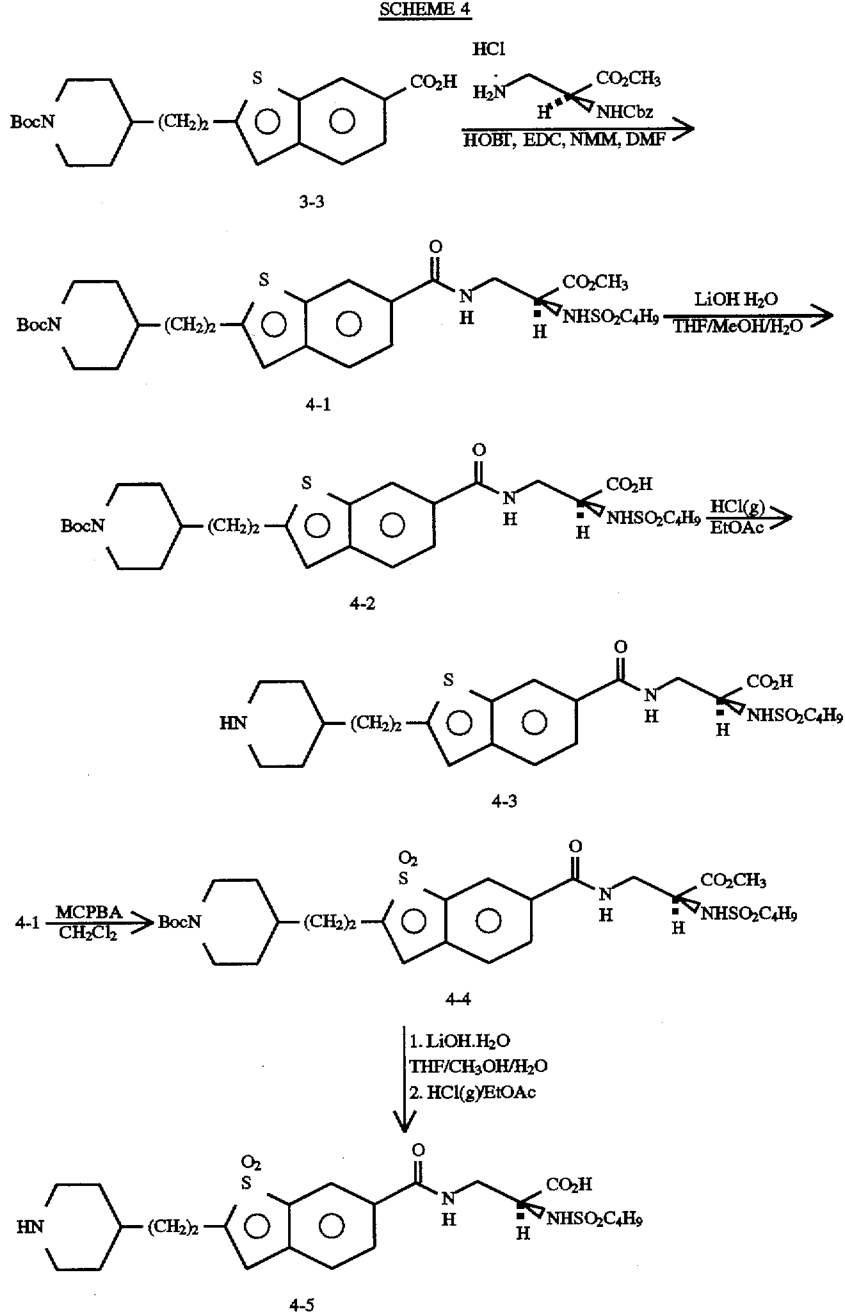

2-[2-(N-t-Butyloxycarbonylpiperidin-4-yl)ethyl] benzothiophene-6-N-[3-(Methyl 2(S)-butylsulfonylaminopropionate)]carboxamide (4-1)

A solution of 3-3 (0.58 g, 0.0015 mol), 5-6 (0.41g, 0.0015 mol) and HOBT (0.22 g, 0.0016 mol) in DMF (20 ml) was treated at room temperature with NMM (0.45 g, 0.0045 mol) followed by EDC (0.34 g, 0.00175 mol) and the resulting mxt. was stirred for 16 hrs.

The solvent was removed, and the residue was diluted with $H_2O$ (150 ml) and extracted with EtOAc. The organic extract was washed with 10% $KHSO_4$ solution, brine, saturated $NaHCO_3$ solution and dried ($NaSO_4$). Solvent removal provided a residue that was purified by flash chromatography on silica gel eluting with $CHCl_3$(98)/MeOH (2) to give pure 4-1. $R_f$ 0.25, silica, $CHCl_3$(98)/MeOH (2).

$^1$H NMR (300 MHz, $CDCl_3$) δ 0.90 (3H, t), 1.18 (2H, m), 1.39 (2H, t), 1.45 (9H, s), 1.50 (2H, m), 1.58–1.85 (6H, m), 2.67 (2H, bt), 2.95 (2H, t), 3.03 (2H, m), 3.83 (3H,s), 3.92 (1H, m), 4.09 (2H, m), 4.36 (1H, m), 5.63 (1H, d), 6.85 (1H, t), 7.02 (1H, s), 7.68 (1H, s), 8.25 (1H, s).

2-[2-(N-t-Butyloxycarbonylpiperidin-4-yl)ethyl] benzothiophene-6-N-[3-(2(S)-butylsulfonylaminopropionic acid)]carboxamide (4-2)

4-1 (0.054 g, 0.0031 mol) was treated with LiOH.$H_2O$ as described for 2-5 to give 4-2. $R_f$ 0.2, silica, $CHCl_3$(95)/MeOH (5).

2-[2-(Piperidin-4-yl)ethyl]benzothiophene-6-N-[3-(2 (S)-butylsulfonylaminopropionic acid)]carboxamide (4-3)

4-2 (0.23 g) was dissolved in EtOAc and treated with HCl (g) as described for 3-6 to give 4-3, $R_f$ 0.3, silica, EtOH(9) /$H_2O$ (1)/$NH_4OH$(1)

$^1$H NMR (300 MHz, $CD_3OD$) δ 0.87 (3H, t), 1.38 (4H, m), 1.75 (5H, m), 2.02 (3H, m), 3.00 (6H, m), 3.38 (2H, bd), 3.60 (1H, m), 3.85 (1H, dd), 4.34 (1H, m), 7.18 (1H, s), 7.77 (2H, m), 8.30 (1H, s).

2-[2-(N-t-Butyloxcarbonylpiperidin-4-yl)ethyl] benzothiophene -S,S-dioxide-6-N-[3-(Methyl 2(S)-butylsulfonylaminopropionate)]-carboxamide (4-4)

A solution of m-chioroperbenzoic acid (0.216 g, 0.001 mol) in $CH_2Cl_2$ (10 ml) at room temperature was treated with 4-1 (0.24 g, 0.4 mmol) and the resulting solution was stirred for 3 hrs. This was diluted with $CH_2Cl_2$ (100 ml), washed with $H_2O$, saturated $NaHCO_3$ solution, brine and dried ($Na_2SO_4$). The solvent was removed and the residue purified by chromatography on silica gel eluting with hexane (35)/EtOAc(65) to give 4-4, $R_f$ 0.35, silica, hexane(35)/ EtOAc (65).

2-[2-(Piperidin-4-yl)ethyl]benzothiophene-S,S-dioxide-6-N-[3-(2(S)-N-butylsulfonylaminopropionic acid)] carboxamide (4-5)

4-4 (0.25 g, 0.39 mmol) was treated with LiOH.$H_2O$ as described for 3-5 to provide the desired acid, $R_f$ 0.3, silica, $CHCl_3$(90)/$CH_3OH$(9)/HOAc(1). This acid was dissolved in EtOAc and treated with HCl (g) as described for 3-6 to give 4-5, $R_f$ 0.25 [(silica, EtOH(10)/$NH_4OH$(1)/$H_2O$ (1)].

$^1$H NMR (300 MHz, $CD_3OD$) δ 0.76 (3H, t), 1.23 (1H, t), 1.40 (4H, m), 1.78 (5H, m), 2.03 (2H, m), 2.67 (2H, t), 3.04 (4H, m), 3.40 (1H, db), 3.61 (1H, m), 4.09 (1H, m), 4.26 (1H, m), 7.18 (1H, s), 7.55 (1H, d), 8.10 (1H, dd), 8.16 (1H, d).

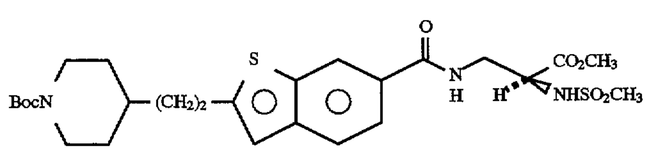

2-[2-(N-t-Butyloxycarbonylpiperidin-4-yl)ethyl] benzothiophene-6-N-(3-[methyl 2(S)-N-methylsulfonylaminopropionate)]carboxamide (4-6)

3-3 (0.234 g, 0.6 mmol) as treated with 5-7 (0.14 g, 0.6 mmol) as described for 4-2 to provide crude 4-6 which was purified by flash chromatography on silica gel eluting with hexane(60)/acetone(40). to provide pure 4-6. $R_f$ 0.4, silica, hexane(60)/acetone (40).

$^1$H NMR (300 MHz, $CDCl_3$) δ 1.15 (2H, m), 1.28 (1H, m), 1.45 (9H, s), 1.73 (4H, m), 2.68 (2H, bt), 2.93 (2H, t), 3.00 (3H, s), 3.82 (3H, s), 3.95 (1H, m), 4.08 (2H, m), 4.39 (1H, m), 5.82 (1H, d), 6.87 (1H, t), 7.02 (1H, s), 7.68 (2H, s), 8.23 (1 H, s).

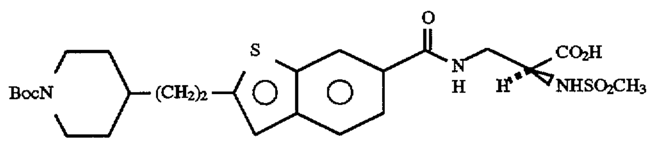

2-[2-(N-t-Butyloxycarbonylpiperidin-4-yl)ethyl] benzothiophene-6-N-[3-(2(S)-methylsulfonylaminopropionic acid)]carboxamide (4-7)

4-6 (0.24 g, 0.42 mmol) was treated with LiOH.$H_2O$ (0.053 g, 1.27 mmol) as described for 4-1 to provide pure 4-7. $R_f$ 0.2, silica, $CHCl_3$(95)/MeOH (5).

$^1$H NMR (300 MHz, $CDCl_3$) δ 1.12 (2H, m), 1.45 (9H, s), 1.64 (4H, m), 2.63 (2H, bt), 2.89 (2H, m), 2.91 (3H, s), 3.80 (1H, m), 3.90 (1H, m), 4.07 (2H, m), 4.36 (1H, m), 6.22 (1H, m), 6.95 (1H, s), 7.40 (1H, m), 7.60 (1H, d), 7.66 (1H, d), 8.20 (1H, s).

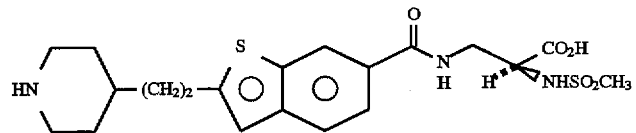

2-[2-(Piperidin-4-yl)ethyl]benzothiophene-6-N-[3-(2(S)-methylsulfonyl-aminopropionic acid)]carboxamide (4-8)

4-7 (0.21 g, 3.79 mmol) was dissolved in EtOAc (25 ml) and treated with HCl (g) at −25° as described for 4-3 to give pure 4-8. $R_f$ 0.45, silica, EtOH(10)/conc $NH_4OH$(1)/$H_2O$ (1).

Calc. for $C_{20}H_{27}N_3O_5S_2$.HCl: C, 49.02; H, 5.76; N, 8.57. Found: C, 48.73; H, 6.00; N, 8.27.

SCHEME 5

2-Substituted-3-Aminopropionates are prepared in the following manner:

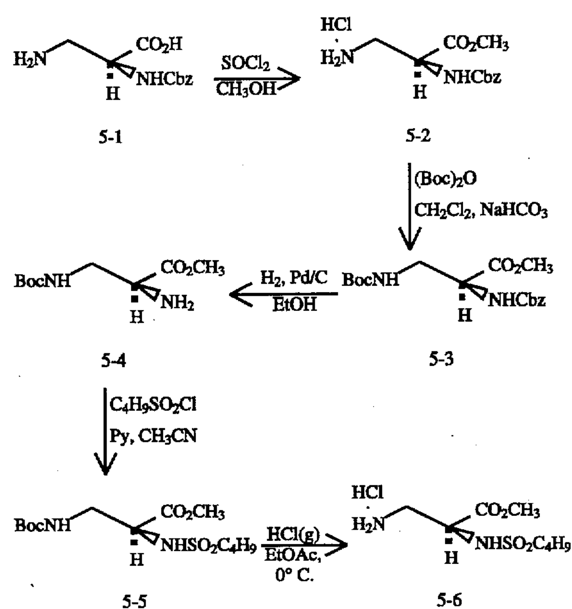

Methyl 2(S)-benzyloxycarbonylamino-3-aminopropionatehydrochloride (5-2)

To a cooled suspension of 2(S)-benzyloxycarbonylamino-3-aminopropionic (Fluka) acid (5-1) (10 g, 0.042 mol) in 150 ml of methanol was added 5.47 g (0.046 mol) of thionyl chloride over 20 minutes. The resulting solution was allowed to stir at room temperature overnight. After ~18 hrs, the solvent was removed in vacuo, and the residual solid was stirred with 150 ml of ether for 0.5 hr. The resulting white solid was collected and air dried to give 5-2.

$^1$H NMR (300 MHz, $CD_3OD$) δ 3.26 (2H, m), 3.45 (1H, dd), 3.77 (3H, s), 4.25 (1H, m), 5.13 (2H, s), 7.37 (5H, m).

Methyl 2(S)-benzyloxycarbonylamino-3-(N-t-butyloxycarbonyl)-aminopropionate (5-3)

To a 2-phase mixture of $CH_2Cl_2$ (500 ml) and saturated $NaHCO_3$ solution (300 ml) was added 28.87 g (0.10 mol) of 5-2. After a few minutes, 21.83 g (0.10 mol) of di-t-butyldicarbonate was added in one portion and the resulting mixture was stirred at room temperature for 4 hrs. The $CH_2Cl_2$ layer was then separated from the aqueous layer, and the aqueous layer was extracted with 300 ml of $CH_2Cl_2$. The combined organic extracts were washed with brine, dried and the solvent removed in vacuo to provide the product as a viscous oil. Trituration of this oil with 300 ml of hexane gave 5-3 as a white solid, m.p. 85°–87°.

$^1$H NMR (300 MHz, $CDCl_3$) δ 1.42 (9H, s), 1.50 (4H, m), 1.62 (1H, m), 3.52 (2H, m), 3.75 (3H, s), 4.41 (1H, m), 4.83 (1H, m), 5.12 (2H, s), 5.78 (1H, m), 7.35 (5H, m).

Methyl 2(S)-amino-3-(N-t-butyloxycarbonyl) aminopropionate (5-4)

To a solution of 6.60 g (0.0187 mol) 5-3 in 150 ml EtOH was added 0.5 g of 10% Pd/C. The resulting mixture was hydrogenated under balloon pressure at r.t. for 4 hrs. The catalyst was filtered off and the solvent removed in vacuo to provide 5-4 as a viscous oil.

$^1$H NMR (300 MHz, $CDCl_3$) δ 1.45 (9H, s), 1.49 (2H, m), 1.59 (2H, m), 3.25 (1H, m), 3.49 (1H, m), 3.58 (1H,m), 3.75 (3H, s), 5.03 (1H, m)

Methyl 2(S)-butylsulfonylamino-3-(N-t-butylcarbonyl)aminopropionate (5-5)

To a solution of 0.400 g (0.00183 mol) of 5-4 in 10 ml of $CH_3CN$ was added 0.226 g (0.00286 mol) pyridine followed by 0.408 g (0.0026 mol) of n-butanesulfonyl chloride. The resulting solution was stirred at room temperature for 2.5 hrs at which time starting material was consumed. The solvent was removed in vacuo and 50 ml of $H_2O$ added to the residual material. This mixture was extracted with 3×50 ml portions of ethyl acetate and the combined extracts washed with brine, dried ($Na_2SO_4$), filtered and concentrated to give 0.5 g of a viscous oil. Trituration to this oil with 25 ml of hexane provided 5-5 as a white, amorphous solid.

$^1$H NMR (300 MHz, $CDCl_3$) δ 0.95 (3H, t), 1.43 (9H, s), 1.48 (2H, m), 1.80 (2H, m), 3.03 (2H, m), 3.52 (2H, t), 3.80 (3H, s), 4.22 (1H, m), 4.99 (1H, bt), 5.48 (1H, bd),

Methyl 2(S)-butylsulfonylamino-3-aminopropionatehydrochloride (5-6)

A cooled (−20° C.) solution of 0.400 g (0.00118 mol) of 5-5 in 25 ml of ethyl acetate was treated with HCL gas for 15 min. The resulting solution was then stoppered and allowed to stir at 0° C. for an additional hour. The solvent and excess HCL were removed in vacuo to give 5-6 as a hygroscopic, yellowish foam.

$^1$H NMR (300 MHz, $CDCl_3$) δ 0.94 (3H, t), 1.44 (9H, s), 1.48 (2H, m), 1.80 (2H, m), 3.04 (2H, m), 3.53 (2H, bt), 3.80 (3H, s), 4.22 (1H, m), 4.93 (1H, m), 5.40 (1H, bd).

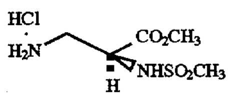

5-7

Methyl 2(S)-Methylsulfonylamino-3-aminopropionatehydrochloride (5-7)

5-7 was prepared as described above for the butylsulfonylamino analog (5-6) using methanesulfonyl chloride at the appropriate stage.

$^1$H NMR (300 MHz, $CD_3OD$) δ 3.07 (3H, s), 3.13 (1H, m), 3.43 (1H, dd), 3.83 (3H, s), 4.96 (1H, m).

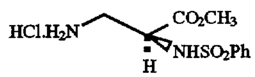

5-8

Methyl 2(S)-Phenylsulfonylamino-3-aminopropionate hydrochloride (5-8)

5-8 was prepared as described above for 5-6 using phenylsulfonylchloride at the appropriate stage.

$^1$H NMR (300 MHz, $D_2O$) δ 3.22 (1H, t), 3.45 (3H, S), 3.51 (2H, m), 4.44 (1H, m), 7.61–7.80 (3H, m), 7.92 (2H, m).

2(S)-Benzylureido-3-aminopropionic acid methyl ester hydrochloride (5-10)

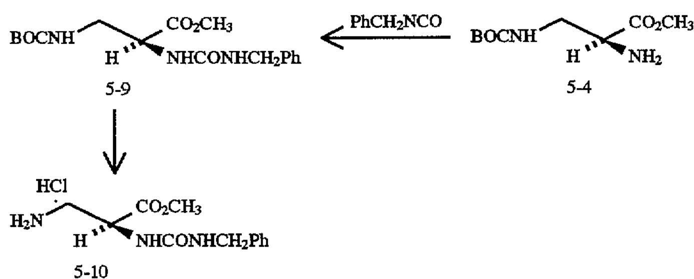

2(S)-Benzylureido-3-(N-t-butyloxycarbonyl) aminopropionic acid methyl ester (5-9)

A solution of 5-4 (1.29 g, 5.9 mmoles) in THF (35 ml) was treated with benzylisocyanate (6.5 mmoles) at room temperature. After stirring for 16 hours, the solvent was removed and the residue was purified by flash chromatography on silica gel eluting with 5% MeOH/EtOAc to give 5-9. $R_f$ 0.7 (silica, 10% MeOH/EtOAc)

$^1$H NMR (300 MHz, $CD_3OD$) δ 1.45 (9H, s), 3.41 (1H, m), 3.53 (1H, m), 3.62 (3H, s), 3.70 (1H, s), 4.32 (3H, m), 5.27 (1H, m), 5.45 (1H, m), 5.90 (1H, m).

2(S)-Benzylureido-3-aminopropionic acid methyl ester hydrochloride (5-10)

Treatment of 5-9 (1.91 g) with HCL gas in EtOAc as described for 5-5 provided pure 5-10. $R_f$ 0.66 (silica, 5% MeOH/$CHCl_3$/$NH_3$)

$^1$H NMR (300 MHz, $CD_3OD$) δ 3.25 (1H, dd) 3.45 (1H, dd), 3.8 (3H, S), 4.4 (2H, S), 4.6 (1H, dd), 7.4 (5H, m).

SCHEME 6

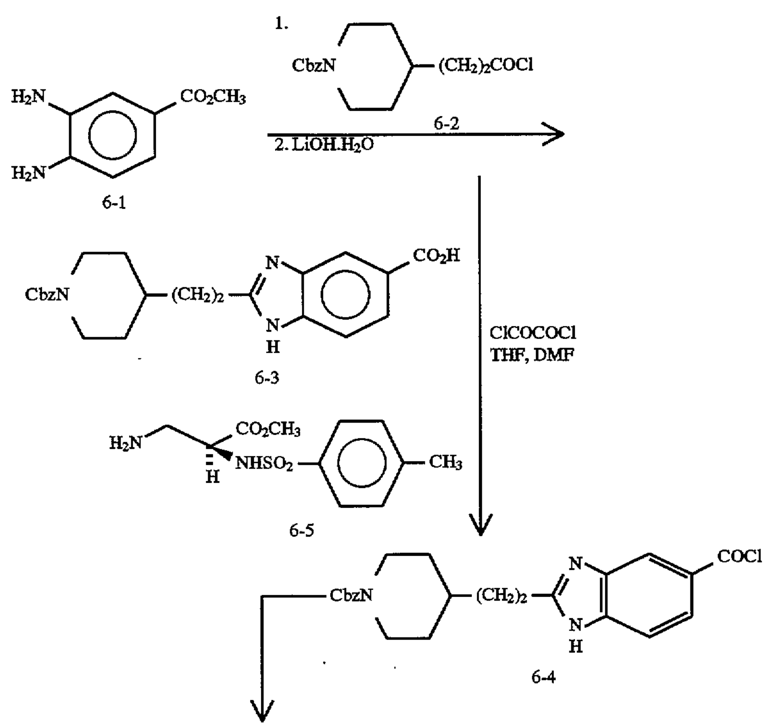

-continued

SCHEME 6

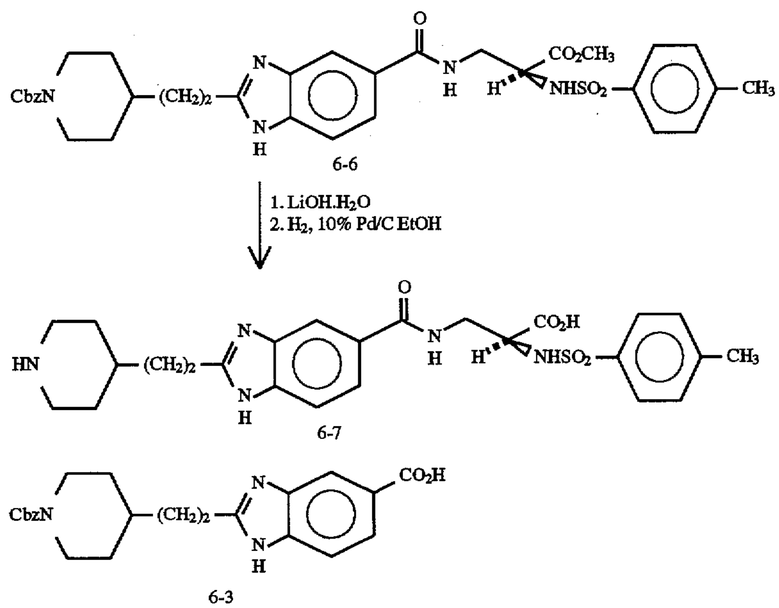

2-[2-(4-N-CBz-Piperidinyl)ethyl]benzimidazole-5-carboxylic acid (6-3)

A solution of methyl-3,4-diaminobenzoate (6.23 g, 37.5 mmol) in 200 ml toluene containing 80 ml of anhydrous pyridine was heated at reflux and a solution containing 3-(4-N-Cbz-Piperidinyl)propionyl-chloride 6-2 (2.90 g, 9.35 mmol) in 60 ml of toluene was added dropwise over 30 minutes. The resulting mixture was refluxed for 20 hours then cooled and evaporated. The residue was redissolved in 500 ml $CH_2Cl_2$, washed successively with 1N HCl (3×50 ml), $H_2O$ (100 ml), saturated $NaHCO_3$(1×100 ml) and brine, then dried over $Na_2SO_4$ filtered and evaporated. This yellow residue was chromatographed on silica gel using 3:1 ethyl acetate/hexane to give the desired ester.

$^1$H NMR ($CDCl_3$) δ 8.25 (s, 1H); 7.95 (d, 1H); 7.55 (d, 1H); 7.36 (m, 5H); 5.17 (s, 2H); 4.18 (d, 2H); 3.93 (s, 3H); 2.92 (t, 2H); 2.76 (m, 2H 1.79 (m, 2H); 1.68 (d, 2H); 1.50 (m, 1H); 1.13 (m, 2H).

This ester (1.68 g, 4.0 mmol) was dissolved in 15 ml THF and treated with $LiOH.H_2O$ (185 g, 4.4 mmol) in 10 ml $H_2O$. The resulting solution was stirred at room temperature for 3.5 hours and then the THF was evaporated at reduced pressure and the aqueous residue acidified with 3N HCl. The resulting oily precipitate was washed twice with $H_2O$ then dissolved in 200 ml EtOAc containing 50 ml $CH_3OH$, dried over $Na_2SO_4$, filtered and evaporated to give 6-3.

$^1$H NMR (DMSO-$d_6$) δ 8.35 (s, 1H); 7.97 (d, 1H); 7.55 (d, 1H); 7.36 (m, 5H); 5.10 (s, 2H); 4.14 (d, 2H); 3.97 (s, 3H); 2.92 (t, 2H); 2.75 (m, 2H); 1.80 (m, 2H); 1.67 (d, 2H); 1.50 (m, 1H); 1.12 (m, 2H).

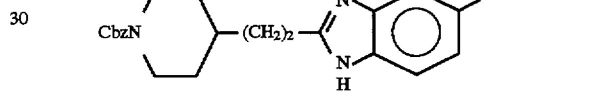

2-[2-(4-N-Cbz-Piperidinyl)ethyl]benzimidazole-5-carbonyl chloride (6-4)

Acid 6-3 (1.5 g, 3.7 mmol) was suspended in 100 ml of THF and 10 gl DMF was added followed by 25 ml of oxalyl chloride. The resulting clear solution was refluxed under $N_2$ for 2.5 hours, then cooled and evaporated. The resulting yellow powder was triturated with hexane, filtered, washed with 50 ml of hexane and dried under vacuum to give 6-4.

$^1$H NMR (DMSO-$d_6$) δ 8.53 (s, 1H); 7.93 (d, 1H); 7.57 (d, 1H); 7.36 (m, 5H); 5.18 (s, 2H); 4.18 (d, 2H); 2.93 (t, 2H); 2.81 (m, 2H); 1.82 (m, 2H); 1.68 (d, 2H); 1.50 (m, 1H); 1.13 (m, 2H).

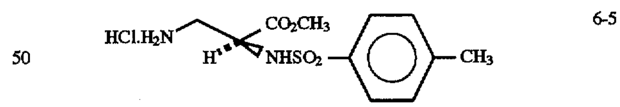

Methyl-2(S)-Toulenesulfonylamino-3-aminopropionate hydrochloride (6-5)

6-5 was prepared as described above for 5-6 using toluene sulfonyl chloride at the appropriate stage.

$^1$H NMR (300 MHz, DMSO-d6) δ 7.73 (d, 2H), 7.19 (d, 2H), 6.13 (d, 1H); 4.53 (m, 1H); 3.73 (s, 3H); 2.76 (m, 2H); 2.26 (s, 3H).

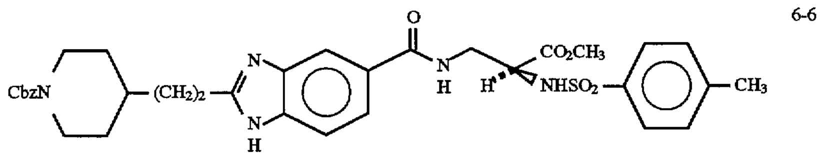

2-[2-(4-N-Cbz-Piperidinyl)ethyl]benzimidazole-5-carbonyl-[2(S)-p-toluenesulfonylamino]-β-methyl ester (6-6)

The acid chloride (329 mg, 0.78 mmol) was dissolved in 15 ml of THF along with 2(S)-toluenesulfonamino-p-alanine methyl ester hydrochloride (6-5) (238 mg, 0.78 mmol). N-methyl morpholine (215 µl, 1.94 mmol) was added and the resulting solution was stirred under $N_2$ for 3.5 h after which the solvent was removed at reduced pressure. The residue was redissolved in 100 ml $CH_2Cl_2$ and washed with 10% $KHSO_4$ (50 ml) then $H_2O$ (50 ml), dried over $Na_2SO_4$ and concentrated. This crude material was purified by flash chromatography on silica using 5% $CH_3OH$/EtOAc as eluent to give pure 6-6.

$^1$H NMR ($CDCl_3$) δ 8.15 (br s, 1H); 8.06 (s, 1H); 7.75 (d, 2H); 7.62 (d, 1H); 7.45 (d, 1H); 7.36 (m, 6H); 7.18 (d, 2H); 5.10 (s, 2H); 4.18 (overlapping m, 3H); 3.82 (m, 2H); 3,64 (s, 3H); 3.01 (t, 2H); 2.76 (m, 2H); 2.28 (s, 3H); 1.79 (m, 2H); 1.68 (d, 2H); 1.50 (m, 1H); 1.13 (m, 2H).

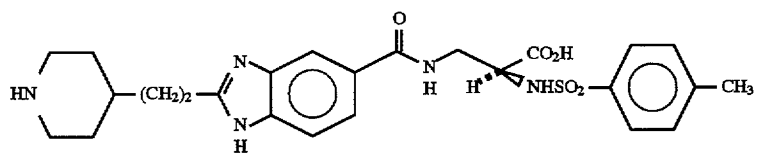

2-[2-(4-Piperidinyl)ethyl]benzimidazole-5-carbonyl [2(S)-p-toluenesulfonylamino]-β-alainine (6-7)

Ester 6-6 (180 mg, 0.273 mmol) was dissolved in 20 ml 50% aqueous THF and treated with LiOH.$H_2O$ (12.56 mg, 0.30 mmol) at room temperature for 2.5 h. Then the organic solvent was evaporated at reduced pressure and the aqueous residue was acidified with 1N HCl and extracted with ethyl acetate (2×50 ml). The combined organic phases were dried ($Na_2SO_4$), filtered and evaporated to give the desired acid.

$^1$H NMR ($CD_3OD$) δ 8.13 (s, 1H); 7.85 (d, 1H); 7.72 (d, 1H); 7.62 (d, 2H); 7.32 (m, 5H); 7.18 (d, 2H); 5.14 (s, 2H); 4.21 (overlapping m, 3H); 3.82 (m, 1H); 3.62 (m, 1H); 3.13 (t, 2H); 2.82 (m, 2H); 2.28 (s, 3H); 1.79 (m, 2H); 1.71 (d, 2H); 1.55 (m, 1H); 1.13 (m, 2H).

This acid (167 mg, 0.258 mmol) was dissolved in 10 ml of absolute ethanol, treated with 20 mg 10% Pd on C, and the mixture was stirred under a $H_2$ filled balloon for 16 h. Next, the catalyst was removed by filtration through Celite and the filtrate evaporated to give pure 6-7, mp 180°–185° (dec.).

$^1$H NMR (DMSO-$d_6$) a 8.15 (br s, 1H); 8.06 (s, 1H); 7.75 (d, 2H); 7.62 (d, 1H); 7.45 (d, 1H); 7.18 (d, 2H); 4.18 (overlapping m, 3H); 3.82 (m, 2H); 3.64 (s, 3H); 3.01 (t, 2H); 2.76 (m, 2H); 2.28 (s, 3H); 1.79 (m, 2H); 1.68 (d, 2H); 1.50 (m, 1H); 1.13 (m, 2H)

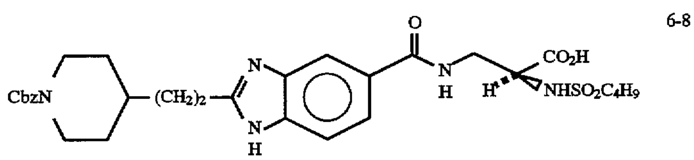

2-[2-(4-N-Cbz-Piperidinyl)ethyl]benzimidazole-5-carbonyl-[2(S)-butylsulfonylamino-β-alanine (6-8)

Treatment of 6-4 with 5-6 as described for 6-6 provided the desired ester which was hydrolyzed with LiOH.$H_2O$, as described for 6-7, to give 6-8.

$^1$H NMR ($CD_3OD$) δ8.08 (s, 1H); 7.75 (d, 1H); 7.53 (d, 1H); 7.36 (m, 6H); 5.10 (s, 2H); 4.20–4.09 (overlapping multiplets, 5H); 3.82 (dd, 1H); 3.62 (dd, 1H); 3.06 (t, 2H); 2.96 (t, 2H); 2.78 (m, 2H); 1.821.62 (overlapping multipiers, 6H); 1.50 (m, 1H); 1.38 (m, 2H); 1.13 (m, 2H); 0.85 (t, 3H).

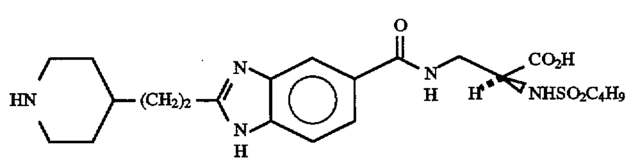

2-[2-(4-Piperidinyl)ethyl]benzimidazole-5-carbonyl-[2(S)-butylsulfonylamino]-β-alanine (6-9)

6-8 (153 mg, 0.256 mmol) was dissolved in 10 ml of absolute ethanol treated with 20 mg 10% Pd on C and mixture stirred under a $H_2$ filled balloon for 16.5 h. Next, the catalyst was removed by filtration through Celite and the filtrate evaporated giving a colorless glass which was vacuum dried over $P_2O_5$ at 50° C. to give pure 6-9, mp 180°–185°.

$^1$H NMR ($CD_3OD$) δ 8.12 (s, 1H); 7.73 (d, 1H); 7.52 (d, 1H); 4.18–4.09 (overlapping multiplets, 3H); 3.81 (dd, 1H); 358 (dd, 1H); 3.32 (d, 2H); 3.03 (t, 2H); 2.95 (t, 2H); 2.78 (m, 2H); 1.82–1.60 (overlapping multiplets, 6H); 1.48 (m, 1H); 1.38 (m, 2H); 1.13 (m, 2H); 0.85 (t, 3H).

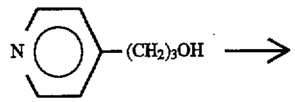

6-10

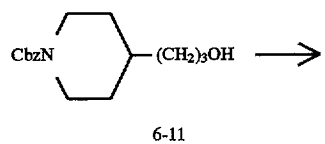

6-11

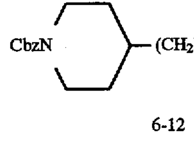

6-12

CbzN (CH₂)₂COCl 6-2

3-(4-N-Cbz-Piperidinyl)propanol (6-11)

Commercially available 4-pyridinepropanol (6-10) (38 g, 277 mmol) was dissolved in 100 ml EtOH/HOAc/$H_2O$ (4:1:1) and treated with 2.0 g 10% Pd/C. This mixture was hydrogenated on a Parr reactor for 24 h at 55 psi. The catalyst was removed by filtration and the filtrate evaporated to give 3-(4-piperidinyl)propyl acetate.

$^1$H NMR ($CDCl_3$) δ 3.65 (t, 2H); 3.52 (d, 2H); 2.81 (t, 2H); 1.75 (d, 2H); 1.72 (m, 2H);1.42 (m, 1H); 1.15 (m, 2H); 1.08 (m, 2H).

A mixture containing this acetate (21.5 g, 107 mmol), $NaHCO_3$ (17.56 g, 208 mmol). 100 ml $H_2O$, and 50 ml $CH_2Cl_2$ was vigorously stirred in a 500 ml flask. To this mixture benzyl chloroformate (16.76 ml, 117 mmol) in 50 ml of $CH_2Cl_2$ was added dropwise over a period of 1 h. The resulting mixture was stirred rapidly for 18 h then the organic phase was removed and the aqueous phase extracted with $CH_2Cl_2$ (2×50 ml). The combined organic extracts were dried over $Na_2SO_4$, filtered, concentrated, and purified by chromatography on silica (1:1 hexane/ethyl acetate) to give 6-11 as a colorless oil.

$^1$H NMR ($CDCl_3$) δ 7.34 (m, 5H); 5.12 (s 2H); 4.09 (d, 2H); 3.65 (t, 2H); 2.81 (t, 2H); 1.84 (d, 2H); 1.72 (m, 2H); 1.42 (m, 1H); 1.21 (m, 2H); 1.08 (m, 2H).

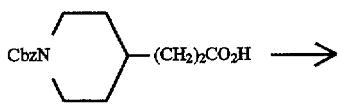

6-12

3-(4-N-Cbz-Piperidinyl)propionic acid (6-12)

6-11 (21.0 g, 73.0 mmol) was dissolved in 50 ml acetone and cooled to 0° C. in an ice bath. Next, a solution of 2.67M Jones reagent (41 ml, 109.5 mmol) was added dropwise over 1 h and the mixture stirred for an additional 1 h after the addition was completed. The excess oxidant was consumed by adding 10 ml of isopropanol and the insoluble precipitate dissolved by the addition of 150 ml of $H_2O$. The acetone was evaporated at reduced pressure and the aqueous residue extracted with $Et_2O$ (3×100 ml). The combined $Et_2O$ layers were extracted with sat. $NaHCO_3$ (2×50 ml), the basic extracts acidified with conc. HCl and extracted with $CH_2Cl_2$ (2×60 ml). The organic extracts were dried ($Na_2SO_4$) and evaporated yielding 6-12 as a colorless viscous oil.

$^1$H NMR ($CDCl_3$) δ 7.34 (m, 5H); 5.12 (s, 2H); 4.09 (d, 2H); 2.81 (t, 2H); 2.42 (t, 2H); 1.84 (d, 2H); 1.72 (t, 2H); 1.42 (m, 1H); 1.08 (m, 2H).

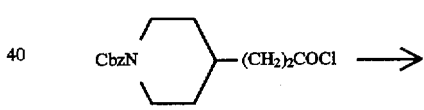

6-2

3-(4-N-Cbz-Piperidinyl)carbonyl chloride (6-2)

6-12 (3.0 g, 10.2 mmol) in 10 ml $CH_2Cl_2$ was treated with oxalyl chloride (1.33 ml, 15.3 mmol) the resulting mixture was stirred at room temperature for 1 h then evaporated at reduced pressure and placed on a high vacuum line for 18 h giving 6-2 as a pale yellow oil.

$^1$H NMR ($CDCl_3$) δ 7.35 (m, 5H); 5.12 (s, 2H); 4.18 (d, 2H); 2.93 (t, 2H) 2.75 (t, 2H); 1.75–1.69 (m, 4H); 1.43 (m, I H); 1.08 (m, 2H).

SCHEME 7

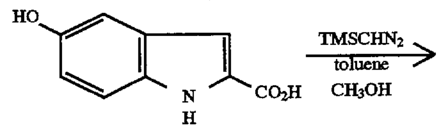

7-1

-continued

SCHEME 7

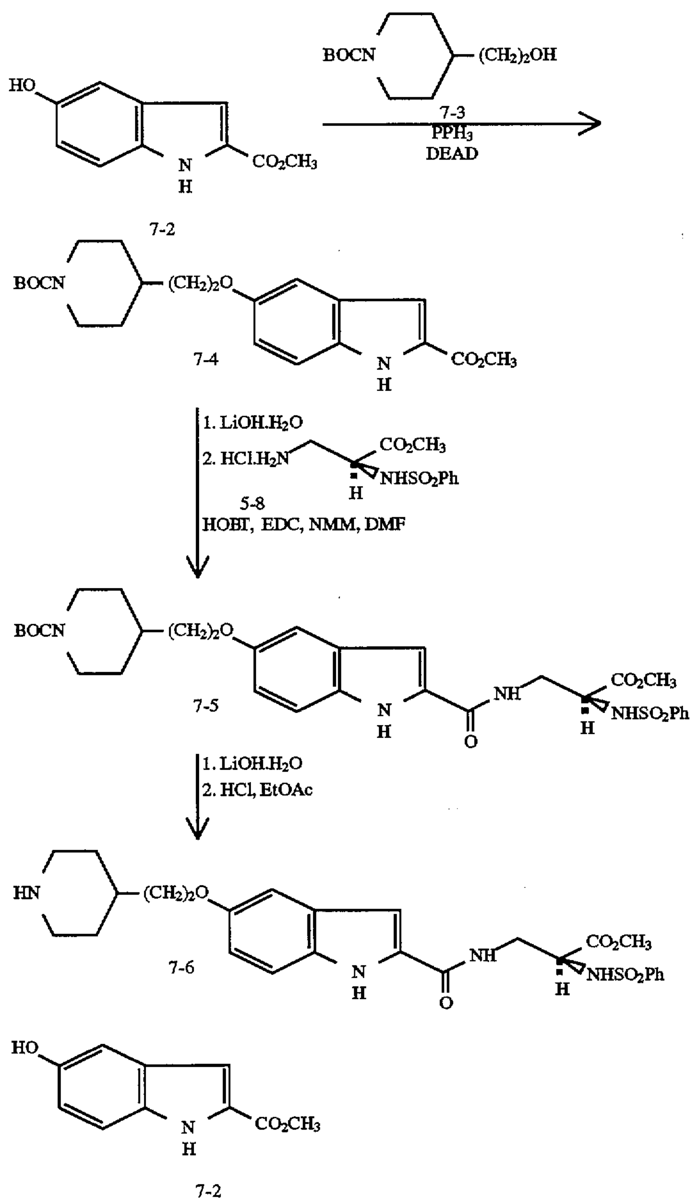

5-Hydroxy-2-indolecarboxylic acid methyl ester (7-2)

5-Hydroxyindole-2-carboxylic acid (Aldrich) (3.54 g, 0.02 mol) in toluene (100 ml)/methanol (25 ml) was treated with $TMSCHN_2$ (0.022 mol) and this solution was stirred at room temperature for 16 hours. The solvent was removed and the residue purified by flash chromatography on silica gel eluting with $CHCl_3$ (95)/MeOH(S) to give pure 7-2, $R_f$ 0.3, silica, $CHCl_3$ (95)/MeOH(5).

$^1$H NMR (300 $MH_3$, $CDCl_3$) δ 3.94 (3H, S), 4.79 (1H, S), 6.94 (1H, dd), 7.09 (2H, m), 7.28 (1H, m), 8.82 (1H, b).

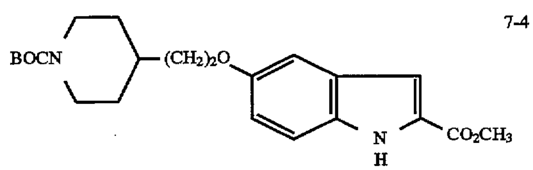

5-[2-(4-N-BOC-Piperidinylethyl)oxy]-2-indolecarboxylicacid methyl ester (7-4)

A solution of 7-2 (0.96 g, 5 mmol) in THF (15 ml) was treated with $PPh_3$ (1.48 g, 5.5 mmol) and after stirring for 10 minutes, diethyl azodicarboxyate (DEAD) (0.96 g, 5.5 mmol) in THF (10 ml) was added dropwise over 1 hour. After stirring at room temperature for 16 hours, the solvent was removed and the residue was taken up in EtOAc, washed with $H_2O$, saturated $NaHCO_3$, brine, 10% $KHSO_4$, brine and dried ($Na_2SO_4$). The solvent was removed and the residue purified by flash chromatography on silica gel eluting with hexane(4)/EtOAc(1) to give pure 7-4.

$^1H$ NMR (300 $MH_3$, $CDCl_3$) δ 1.20 (2H, m), 1.45 (9H, s), 1.59 (1H, s), 1.77 (4H, m), 2.71 (2H, bt), 3.92 (3H, s), 4.06 (3H, m), 6.98 (1H, dd), 7.07 (1H, m), 7.12 (1H, m), 7.31 (1H, d).

5-[2-(4-Piperidinylethyl)oxy]2-indolecarbonyl-2(S)-phenylsulfonylamino-β-alanine (7-6)

7-5 (0.33 g, 0.53 mmol) was treated with $LiOH.H_2O$ (0.066 g, 1.57 mmol) as described for 4-1 to provide the desired acid. $R_f$ 0.1, silica $CHCl_3$ (95)/($CH_3OH$(5)/HOAc (1).

This acid was dissolved in EtOAc, cooled to −25° and treated with HCl gas as described for 4-3 to give pure 7-6.

7-5

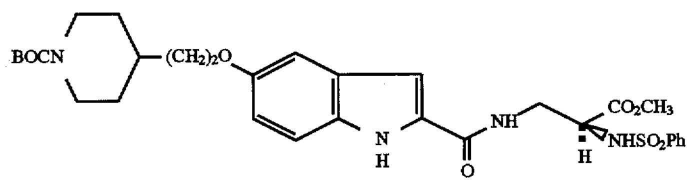

5-[2-(4-N-BOC-Piperidinylethyl)oxy]-2-indolecarbonyl-2(S)-phenyl-sulfonylamino-β-alanine (7-5)

7-4 (0.77 g, 1.9 mmol) was treated with $LiOH.H_2O$ (0.24 g, 5.7 mmol) as described for 4-1 to give the desired acid. $R_f$ 0.5, silica, $CHCl_3$ (95)/MeOH (5).

This acid (0.226 g, 0.58 mmol) was dissolved in DMF and a room temperature was treated successively with 5-8 (0.17 g, 5.8 mmol), HOBT (0.086 g. 0.64 mmol), NMM (0.176 g, 1.74 mmol), and EDC (0.13 g, 0.68 mmol). After stirring for 24 hours, the solvent was removed and the residue was taken up in $H_2O$ (50 ml)/EtOAc(100 ml) and this organic phase was washed with 10% $KHSO_4$, brine, saturated $NaHCO_3$, brine and dried ($Na_2SO_4$). The solvent was removed and the residue purified by flash chromatography on silica gel eluting with $CHCl_3$(95)/MeOH(5) to give pure 7-5.

$^1H$ NMR (300 $MH_3$, $CD_3OD$) δ 1.13 (2H, m), 1.45 (9H, s), 1.73 (4H, m), 2.77 (2H, bt), 3.49 (3H, s), 3.57 (1H, m), 3.68 (1H, m), 4.03 (3H, m), 4.22 (1H, m), 6.89 (2H, m), 7.04 (1H, m), 7.30–7.43 (4H, m), 7.80 (2H, m).

$^1H$ NMR (300 $MH_3$, $CD_3OD$) δ 1.48 (2H, m), 1.80 (2H, m), 1.90–2.08 (3H, m), 3.00 (2H, dr), 3.39 (2H, d), 3.54 (1H, m), 3.73 (1H, dd), 4.08 (2H, m), 4.19 (1H, m), 6.88 (2H, m), 7.09 (1H, m), 7.36 (4H, m), 7.82 (2H, m).

7-6

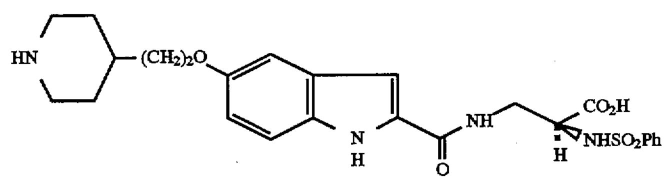

SCHEME 8

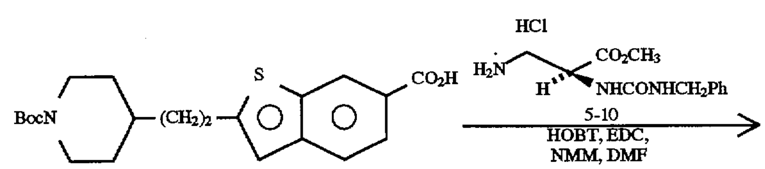

-continued
SCHEME 8

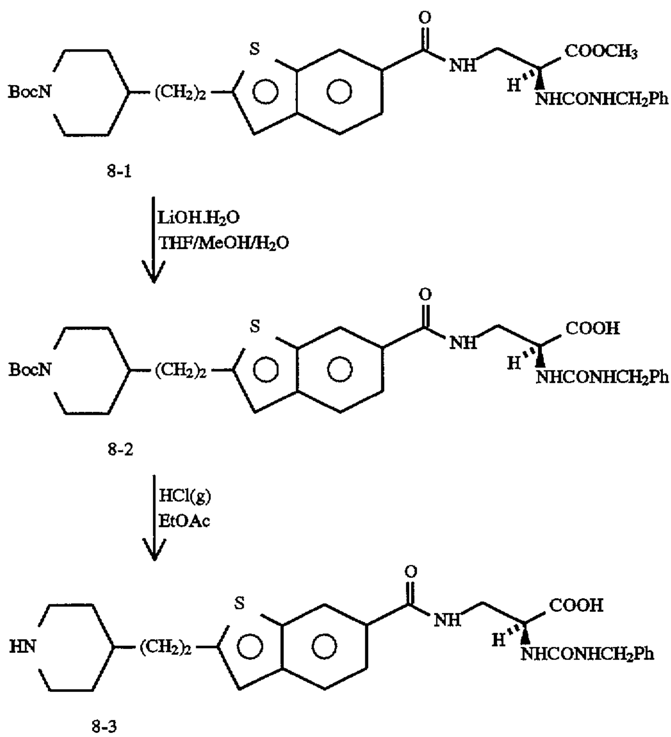

2-[2-(N-t-Butyloxycarbonylpiperidin-4-yl)ethyl] benzothiophene-6-N-[3-(Methyl-2(S)-benzyureidopropionate]carboxamide (8-1)

A solution of 3-3 (0.234 g, 0.0006 mol.), 2-15 (0.173 g, 0.0006 mol.) and HOBT (0.089 g, 0.00066 mol) in DMF (20 ml) was treated with NMM (0.182 g, 0.0018 mol) and EDC (0.144 g, 0.00075 mol) as described for 4-1 to give 8-1 $R_f$ 0.46, silica, $CHCl_3$ (95)/MeOH (S).

$^1$H NMR (300 MHZ, $CDCl_3$) δ 1.07–1.23 (2H, m), 1.47 (9H, s), 1.60–1.80 (4H, m), 2.57–2.75 (2H, bt), 2.85–3.0 (2H, t), 3.71 (3H, s), 3.73–3.90 (2H, bm), 4.00–4.18 (2H, bd), 4.29 (2H, s), 4.67–4.80 (1H, t), 5.40–6.50 (2H, vb), 7.00 (1H, s), 7.10–7.23 (5H, bs) 7.47–7.72 (3H, m), 8.20 (1H, s).

2-[2-(N-t-Butyloxycarbonylpiperidin-4-yl)ethyl] benzothiophene-6-N-[3-(2(S)-benzylureidopropionic acid]carboxamide (8-2)

8-1 (0.209 g, 0.000326 mole) was treated with $LiOH.H_2O$ as described for 2-5 to give 8-2.

$^1$H NMR (300 MHZ, $CDCl_3$) δ 1.04–1.25 (2H, m), 1.45–1.60 (1H, m), 1.45 (9H, s), 1.60–1.82 (4H, m), 2.56–2.76 (2H, bt), 2.80–3.00 (2H, t), 3.68–3.95 (2H, m), 3.97–4.32 (4H, m), 4.46–4.60 (1H, b), 6.00–6.40 (1H, b), 6.60–6.85 (1H, b), 6.94 (1H, s), 7.00–7.23 (5H, m), 7.50–7.67 (2H, dd) 7.70–7.85 (1H, b), 8.14 (1H, s).

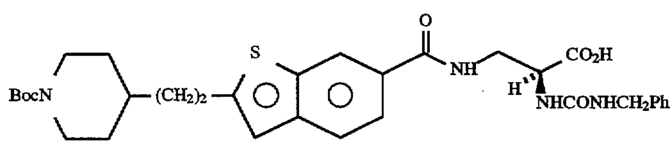

8-2

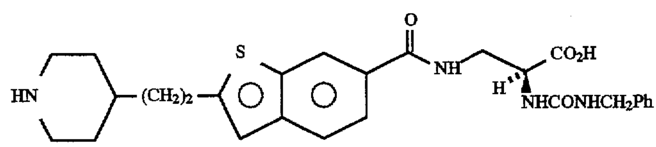

2-[2-(Piperidin-4-yl)ethyl]benzothiophene-6-N-[3-(2 (S)-benzylureido-propionic acid]carboxamide (8-3)

8-2 was suspended in EtOAc and treated with HCl (g) as described for 3-5 to give 8-3. $R_f$ 0.52, silica, EtOH(10)/—$H_2O$ (1)/—$NH_4OH$ (1).

$^1H$ NMR (300 MHz, $CD_3OD$) a 1.45–1.55 (2H, m) 1.62–1.94 (3H, m), 1.96–2.12 (2H, 6d), 2.88–3.12 (4H, m), 3.30–3.45 (2H, m), 3.70–3.85 (2H, t), 4.20–4.37 (2H, q), 4.58–4.67 (1H, dd), 7.02–7.25 (6H, m), 7.72 (2H, s), 8.25 (1H, s).

In addition to those compounds specifically exemplified above, additional compounds of the present invention are set forth in tabular form below. These compounds are synthesized by use of the synthetic mutes and methods described in the above Schemes and Examples and variations thereof well known to those of ordinary skill in the art, and not requiring undue experimentation. All varibles listed in the Tables below are with reference to the following generic structure:

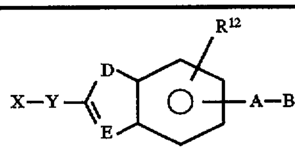

| X | Y | D | E | $R^{12}$ | A | B |
|---|---|---|---|---|---|---|
| $CH_3NH$ | $(CH_2)_5SO_2$ | O | N | $CH_3$ | O<br>‖<br>CNH | $CO_2H$<br>$NHCH_3$ |
| NH<br>‖<br>$H_2NC$—NH | $(CH_2)_3O$ | S | N | F | O<br>‖<br>$CN(CH_3)$ | $CH_3$<br>$CO_2H$<br>NHCPh<br>‖<br>O |
| $CH_3$<br>N<br>‖<br>$H_2NC$—NH | $(CH_2)_2OCH_2$ | CH | O | $CH_2CF_3$ | CH=CH | $CH_3$ $CH_3$<br>$CO_2H$ |
| NH<br>‖<br>$H_2NC$—NH | $CH_2SO_2(CH_2)_2$ | CH | N | $CH_2OCH_3$ | C≡C | H $NHSO_2Ph$<br>$CO_2H$ |
| NH<br>‖<br>$PhCH_2NHCNH$ | O<br>‖<br>$(CH_2)_2C$ | O | CH | $CH_2CO_2Me$ | $CH_2SO_2NH$ | H $NHCOCH_3$<br>$CO_2H$ |
| NH<br>‖<br>$H_2NC$ | $(CH_2)_2$ | S | CH | H | O<br>‖<br>NHC | $CO_2H$<br>H $CH_2NH$<br>\|<br>$SO_2Ph$ |
| NH<br>‖<br>$H_2NC$ | S<br>$CH_2$ $CH_2$ | O | N | $OC_2H_5$ | $CH_3$<br>\|<br>$CH_2C$=CH | H Ph<br>$CO_2H$ |
| NH<br>‖<br>$CH_3NHC$ | $CH_2S$ | NH | N | H | $NHSO_2$ | $CO_2H$<br>H $NHCNHCH_3$<br>‖<br>O |

-continued

X—Y—(D, E ring)—(benzene ring, $R^{12}$)—A—B

| X | Y | D | E | $R^{12}$ | A | B |
|---|---|---|---|---|---|---|
| $H_2NC(=NH)$ | CH=CH | O | CH | Ph | $CH_2$ | H, $CO_2H$, $CH_2C(=O)CH_2Ph$ |
| $H_2N$ | $(CH_2)_6$ | CH | N | $OCH_3$ | $C{\equiv}CH_2$ | $CH_2$, $CO_2CH_3$, $NH_2$ |
| N (pyridyl ring) | $OCH_2$ | NH | N | H | $C(=O)NH$ | H, $CO_2CH_3$, $NHSO_2C_4H_9$ |
| N, N (ring) | $CH_2$ | O | N | $CH_3$ | $NHC(=O)$ | H, $CO_2H$, $CH_2SO_2$—(phenyl)—$CH_3$ |
| HN (ring) | $CH_2C(=O)$ | S | CH | H | $SO_2CH_2$ | H, $CO_2H$, $NHSO_2NHC_4H_9$ |
| HN (ring) | $C(=O)CH_2$ | O | CH | Cl | $C{\equiv}C$ | H, $CO_2CH_3$, $NHSO_2CH_2$—(N ring) |
| HN (ring) | $CH_2CH_2CH_3$ | CH | N | H | $CH_3$, $NC(=O)CH_2$ | H, $CO_2H$, $NHC(=O)$—(S ring) |

What is claimed is:

1. A compound of the invention having the formula:

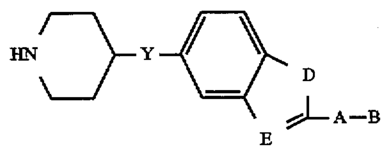

or a pharmaceutically acceptable salt thereof, wherein:

Y is $(CH_2)_mO$, $-NHC(=O)-$,

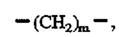

$-C(=O)-$, or

-continued $-C(=O)NH-$, wherein m is an integer chosen from 0, 1, 2, 3, 4, 5 and 6;

E is CH or N;

D is O, S or NH;

A is $-NHC(=O)-$, $-C(=O)-$, $-C(=O)NH-$, or $(CH_2)_n$;

wherein n is an integer chosen from 0, 1, 2, 3, 4, 5 and 6;

B is

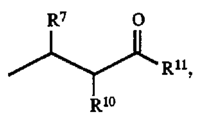

wherein $R^7$ is hydrogen, $C_{1-8}$alkyl, or aryl;

$R^{10}$ is carboxy$C_{0-6}$alkyl, benzyloxycarbonylamino, $C_{1-8}$alkylsulfonylamino, phenyl $C_{0-8}$alkylaminocarbonylamino $C_{0-6}$ alkyl, hydrogen, arylsulfonylamino, wherein aryl is unsubstituted or substituted with halogen, or alkylarylsulfonylamino; and $R^{11}$ is OH or $C_{1-8}$alkyloxy.

2. A compound of claim 1, or a pharmaceutically acceptable salt thereof, wherein A is $(CH_2)_n$ or $$-\overset{O}{\overset{\|}{C}}NH-.$$

3. A compound of claim 2, or a pharmaceutically acceptable salt thereof, wherein Y is $—CH_2O—$ or $—CH_2CH_2O—$; and B is $-CH_2CH(COOH)(NHSO_2Ph)$, $-CH_2CH_2COOH$,

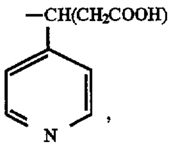

$-CH(CH_3)(CH_2COOH)$,

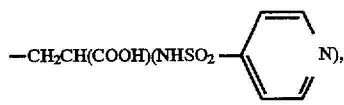

$-CH_2CH(COOH)(NHSO_2PhCH_3)$, or $-CH_2CH(COOH)(NHSO_2PhBr)$.

4. A compound of claim 3, or the pharmaceutically acceptable salt thereof, which is 5-[2-(4-Piperidinylethyl) oxy]-2-indolecarbonyl-2(S)-phenylsulfonylamino-β-alainine.

5. A composition for inhibiting the binding of fibrinogen to blood platelets in a mammal, comprising a compound of claim 1 and a pharmaceutically acceptable carrier.

* * * * *